United States Patent [19]

Antonuk et al.

[11] Patent Number: 5,262,649

[45] Date of Patent: * Nov. 16, 1993

[54] THIN-FILM, FLAT PANEL, PIXELATED DETECTOR ARRAY FOR REAL-TIME DIGITAL IMAGING AND DOSIMETRY OF IONIZING RADIATION

[75] Inventors: Larry E. Antonuk, Ann Arbor, Mich.; Robert A. Street, Palo Alto, Calif.

[73] Assignees: The Regents of the University of Michigan, Ann Arbor, Mich.; Xerox Corporation, Palo Alto, Calif.

[*] Notice: The portion of the term of this patent subsequent to Jan. 7, 2009 has been disclaimed.

[21] Appl. No.: 817,364

[22] Filed: Jan. 6, 1992

Related U.S. Application Data

[63] Continuation-in-part of Ser. No. 681,650, Apr. 8, 1991, Pat. No. 5,079,426, which is a continuation of Ser. No. 403,450, Sep. 6, 1989, abandoned.

[51] Int. Cl.$^5$ .............................................. G01T 1/24
[52] U.S. Cl. .......................... 250/370.09; 250/370.11; 250/370.14
[58] Field of Search .................. 250/370.09, 370.11, 250/370.14

[56] References Cited

U.S. PATENT DOCUMENTS

| Re. 32,164 | 5/1986 | Kruger | 378/19 |
|---|---|---|---|
| 4,250,385 | 2/1981 | Luderer et al. | 250/370.11 |
| 4,288,264 | 9/1981 | Haque | 156/67 |
| 4,525,628 | 6/1985 | DiBianca et al. | 250/361 R |
| 4,626,688 | 12/1986 | Barnes | 250/361 R |
| 4,672,454 | 6/1987 | Cannella et al. | 358/213.11 |
| 4,679,212 | 7/1987 | Hynecek | 357/24 |

(List continued on next page.)

FOREIGN PATENT DOCUMENTS

| 0163956 | 12/1985 | European Pat. Off. |
| 0239808 | 3/1987 | European Pat. Off. |
| 0287197 | 10/1988 | European Pat. Off. |
| 3829912 | 3/1989 | Fed. Rep. of Germany |

OTHER PUBLICATIONS

Naruse et al, IEEE Transactions on Nuclear Science, vol. 36, No. 2, Apr. 1989, pp. 1347-1352. ("Metal/Amorphous Silicon Multilayer Radiation Detectors").

(List continued on next page.)

Primary Examiner—Carolyn E. Fields
Attorney, Agent, or Firm—Oblon, Spivak, McClelland, Maier & Neustadt

[57] ABSTRACT

A thin-film, flat panel, pixelated detector array serving as a real-time digital imager and dosimeter for diagnostic or megavoltage X rays or gamma rays, including a plurality of photodiodes made of hydrogenated amorphous silicon arrayed in columns and rows upon a glass substrate. Each photodiode is connected to a thin film field effect transistor also located upon the glass or quartz substrate. Upper and lower metal contacts are located below and above the photodiodes to provide the photodiodes with a reverse bias. The capacitance of each photodiode when multiplied by the resistance of the field effect transistor to which it is connected yields an RC time constant, $\tau_{RC}$, sufficiently small to allow fluoroscopic or radiographic imaging in real time. Specifically, $$\tau_{RC} \leq \frac{100 \cdot P}{L \cdot IFPS \cdot \ln(SN)}$$

where
P = the pixel-pixel pitch in $\mu$m, where $\sim 25 \leq p \leq \sim 10{,}000$,
L = the length, in cm, of one column of pixels sensors of the array, where $\sim 2 \leq L \leq \sim 60$,
IFPS = instantaneous frame rate per second which is the effective rate at which the array is being read-out, where $\sim 1 \leq IFPS \leq \sim 500$, and
SN = the inverse of the degree to which each pixel sensor needs to be sampled and thus recharged, where $\sim 10 \leq SN \leq \sim 10{,}000$.

33 Claims, 6 Drawing Sheets

| | | |
|---|---|---|
| 4,707,608 | 11/1987 | DiBianca .................. 250/389 |
| 4,785,186 | 11/1988 | Street et al. .............. 250/370.14 |
| 4,799,094 | 1/1989 | Rougeot .................. 357/31 |
| 4,823,369 | 4/1989 | Guenther et al. ............ 378/22 |
| 4,982,095 | 1/1991 | Takahashi et al. ........... 250/370.11 |
| 5,017,990 | 5/1991 | Chen et al. ............... 357/34 |
| 5,019,711 | 5/1991 | Antonuk .................. 250/385.1 |
| 5,079,426 | 1/1992 | Antonuk et al. ............ 250/370.09 |

OTHER PUBLICATIONS

"The Dynamic Response of Hydrogenated Amorphous Silicon Imaging Pixels", Materials Research Society Symposium Proceedings, vol. 219, pp. 173-178. (Yorkston et al.), 1991.

Perez-Mendez et al, Materials Research Society, vol. 149, 1989, pp. 621-632. ("The Application of Thick Hydrogenated Amorphous Silicon Layers to Charged Particle and X-Ray Detection").

V. Perez-Mendex, et al, "Signal Recombination Effects and Noise in Amorphous Silicon Detectors", Nuclear Instrument and Methods in Physics Research A260 (1987); 195-200, Elsevier Science Publishers B.V.

I. D. French, et al., "The Effect of γ-Irradiation on Amorphous Silicon Field Effect Transistors", Applied Physics A31, 19-22, 1983, Springer-Verlag.

H. C. Tuan, "Amorphous Silicon Thin Film Transistor and its Application to Large-Area Electronics", Mat. Res. Soc. Symp. Proc. vol. 33 (1984) Elsevier Science Publishing Company, Inc., pp. 247-257.

Int. J. Radiation Onology Biol., Phys., vol. 18, pp. 1477-1484. (Wong et al, "On-Line Radiotherapy Imaging with an Array of Fiber-Optic Image Reducers"), 1990.

RadioGraphics, vol. 9, No. 6, Nov. 1989. ("Radiography and Fluoroscopy 1920 to the Present"; J. S. Krohmer) pp. 1129-1153.

1991 IEEE Nuclear Science Symposium and Medical Imaging Conference, "Radiation Response Characteristics of Amorphous Silicon Arrays for Megavoltage Radiotherapy Imaging" (Antonuk et al).

"Signal, Noise, and Readout Considerations in the Development of Amorphous Silicon Photodiode Arrays for Radiotherapy and Diagnostic X-ray Imaging", SPIE vol. 1443 Medical Imaging V: Image Physics (1991) pp. 108-119. (Antonuk et al).

"Light Response Characteristics of Amorphous Silicon Arrays for Megavoltage and Diagnostic Imaging", Materials Research Society Symposium Proceedings, vol. 219, 1991, pp. 531-536. (Antonuk et al), 1991.

MANNER OF OPERATION

1 FLOURSCOPIC MODE

THIN-FILM, FLAT PANEL, PIXELATED DETECTOR ARRAY FOR REAL-TIME DIGITAL IMAGING AND DOSIMETRY OF IONIZING RADIATION

This invention was made with Government support under Grant R01 CA51397 award by the National Institute of Health. The Government has certain rights in the invention.

CROSS REFERENCE TO RELATED APPLICATIONS

This application is a continuation-in-part application of parent U.S. application Ser. No. 07/681,650 filed Apr. 8, 1991, now U.S. Pat. No. 5,079,426, which was a continuation of abandoned U.S. patent application 07/403,450 filed Sep. 6, 1989.

BACKGROUND OF THE INVENTION

1. Field of the Invention:

The present invention pertains generally to the field of radiation detecting devices and, more particularly, to the field of real-time digital radiation imaging devices.

2. Discussion of the Background:

There are several instances in modern megavoltage radiotherapy and diagnostic x-ray imaging where real-time imaging of high energy photons is a highly useful and critically important technique.

In external beam megavoltage radiation therapy, high energy beams of gamma rays or X rays are used to irradiate a target volume containing tumorous tissue. These high energy photons are typically obtained from either a radioactive 60-Co source (1.17 MeV and 1.33 MeV gamma rays) or produced by means of an accelerator which generates x-ray bremsstrahlung photons beams with energies from 3 MV to 50 MV. In such therapy, it is highly desirable that the maximum dose be delivered to the target volume and the minimum dose be delivered to the surrounding tissue. Prior to treatment, which typically consists of irradiating the patient on a daily basis for several weeks, the patient undergoes a number of preparatory steps in order to identify the region to be irradiated and to determine a "treatment plan" specifying exactly how this irradiation is to be performed. Often, one of these steps is to place the patient on a "treatment simulator", which simulates the motions and geometry of the therapy machine, and which provides fluoroscopic and radiographic diagnostic x-ray images of the patient. The simulator thus provides a means to simulate a treatment to a patient using diagnostic x-rays in place of megavoltage radiation. During simulation the fluoroscopic x-ray images provide a real-time means of simultaneously observing patient anatomy while the patient position is manipulated. In this fashion, a desired patient orientation with respect to the simulated treatment beam is achieved. After simulation, x-ray images recorded during the simulation can then be used to develop a treatment plan for the patient. The goal of this treatment plan is to decide exactly how to perform the actual treatment, i.e., what geometric and dosimetric combination of megavoltage beams to use to satisfactorily irradiate the target region but spar the surrounding normal tissues. Once a treatment plan has been determined, often with the assistance of a computer which allows, among other things, manipulation of the simulation information as well as CT or other imaging information, the patient is typically taken back to the simulator for a verification-simulation in order to verify the geometric correctness of the plan.

When the patient is brought into the treatment room, it is highly desirable, prior to treatment, to verify that the orientation of the patient with respect to the treatment beam closely coincides with the setup achieved in the simulator room. Once verified, the prescription dose can be delivered to the target volume. The achievement of this goal is complicated by the fact that the patient anatomy moves due to both voluntary and involuntary patient motions. Such complications encourage the possibility of delivering too little dose to the target region and/or overdosing the surrounding tissues. In addition, for treatment machines which use a computer controlled scanning treatment beam, there is the additional uncertainty of whether the beam is correctly directed on a burst by burst basis.

The above problems can be overcome by real-time imaging of the megavoltage photon beam. Several real-time imagers are being developed around the world. A real-time megavoltage imager has been developed by H. Meertens at the Netherlands Cancer Institute in Amsterdam which is disclosed in European Patent Application 0196138 which corresponds to U.S. Pat. No. 5,019,711. The Meertens' device operates on the principle of a scanning liquid ionization chamber. However, the Meertens' device is able to detect the imaging signal only over a fraction of the field of view at a given time.

Radiation detecting devices are taught in U.S. Pat. Nos. Hynecek, 4,679,212; Luderer et al., 4,250,385; DiBianca, 4,707,608; Haque, 4,288,264; Kruger, Re. 32,164; Barnes, 4,626,688; and DiBianca et al., 4,525,628; however, these detectors do not make possible real-time imaging for megavoltage photons.

Efforts to develop imagers based on camera-fluoroscopy combinations have produced images of greatly varying quality at rates ranging from four images a second to one image every eight seconds. Such systems have the merit that they are able to detect the imaging signal over the entire field of view simultaneously. However, a camera's expensive and delicate imaging electronics would be irreversibly damaged after approximately 10 to 130 kilorads of dose. Thus, a mirror is used to reflect the light produced by a metal-phosphor screen combination to a camera sitting outside of the direct radiation field. This makes necessary the presence of a bulky light box located in the vicinity of the treatment table where such obstructions are highly undesirable. Furthermore, as the camera is located 2 to 3 feet from the screen and as the target of the camera is small relative to the screen, only a very small amount of light emitted by the screen is utilized by the camera, less than 1%. Consequently, the image quality is limited by the light collection stage rather than by the high-energy quanta detected in the metal-phosphor screen which results in images that are less than optimal.

Recently, another camera-fluoroscopy megavoltage imager consisting of tightly packed, tapered, optical fibers has been reported in Int. J. Radiation Oncology Biol., Phys., Vol 18, pages 1477 to 1484. The fibers make up a 40×40 cm² surface, 12 cm thick, which sits in the beam behind a metal-phosphor screen and "pipes" the light to a video camera. The optical fibers are bunched together in bundles of 1.5×1.5 cm² at the input end and the imager has a thickness of 12 cm. Unfortunately, this system has a light collection efficiency no greater than that of the mirror-camera systems and, like those systems, is rather bulky.

In the optical megavoltage imaging systems discussed above, considerably less than 1% of the visible light photons emitted by the phosphor layer are converted into signal. As a direct consequence, the quantum sink is the light collection stage rather than the stage where X rays are converted to high-energy electrons which enter into the phosphor. Thus, the quality and speed of imaging in the above systems are adversely affected. Moreover, the bulkiness of both the camera-mirror and the optical fiber fluoroscopic imaging systems compromises the clinical utility of these imaging devices.

In diagnostic x-ray imaging, the object to be imaged is placed between the x-ray source and an x-ray receptor. The X rays are generated by an x-ray tube and the range of x-ray energies used corresponds to peak tube voltages of $\sim 20$ kVp to $\sim 150$ Kvp.

Diagnostic x-ray imaging may be divided into two modes, radiographic and fluoroscopic. In current radiographic imaging, single or multiple x-ray images are recorded from an x-ray irradiation in a fashion requiring some intermediate step (such as film development) before the image or images can be viewed. Thus the image or images are not available for presentation immediately after the irradiation, i.e., they are not available within a few seconds. Since the object to be imaged may be subject to motion, the objective of such imaging is usually to capture each image in an interval sufficiently short so as to freeze the motion. In fluoroscopic imaging, a series of consecutive images are produced and presented to an observer during the course of an irradiation allowing the object to be imaged in real-time.

In a similar fashion, radiotherapy imaging may also be divided into radiographic and fluoroscopic modes. A single image of the patient may be obtained prior to the main daily treatment with an amount of radiation small compared to the main treatment dose. Alternatively, a single image may be obtained using the entire treatment dose. Both of these forms of imaging are essentially radiographic modes of acquiring an image. Alternatively, a series of consecutive images may be obtained and displayed during irradiation with all or a fraction of the treatment dose. This is clearly a fluoroscopic mode of imaging.

Radiographic and fluoroscopic x-ray imaging (also called radiography and fluoroscopy) have been under continual development since the discovery of X rays in 1895. Many summaries of the developments in this field exist and a concisely written recent one is to be found in RadioGraphics, Volume 9, Number 6, November 1989.

Currently, most diagnostic radiographic imaging is performed using film-screen systems in which x-ray film is placed next to one or between two phosphor screens which convert the X rays to light which exposes the film. The film then must be developed and the image is then viewed directly from the film and/or the film may be digitized for presentation on a monitor. A second manner of producing radiographic images is by means of so-called scanning-laser-stimulated luminescence (RadioGraphics, Volume 9, Number 6, November 1989, page 1148). In this method, plates containing photostimulable phosphors are irradiated in a manner analogous to film. The phosphors are then "read out" by means of a laser with direct conversion of the signal to digital form. Both film and photostimulable phosphors offer practical and useful means of acquiring radiographic images. However, neither method allows presentation of the image immediately after the irradiation since time is required either for film development or for laser scanning. Film development typically takes $\sim 90$ seconds while laser scanning takes several minutes and several more minutes can be spent going to and from the film processor or laser scanner. Moreover, while an x-ray tube may be quite portable, the film processor and laser scanner are far less so. Finally, for high quality film development, the temperature and quality of the chemicals in the film processor must be closely monitored. It would be highly desirable to develop an imaging technology which allowed immediate presentation of the radiographic image after irradiation meaning within a couple of seconds. This would provide quick feed-back to the operator taking the image letting the operator immediately judge whether the image is of sufficient quality or whether a retake is necessary. This would greatly reduce the time and expense associated with radiographic imaging. Furthermore, an electronic imager could have built-in controls so as to help assure that the irradiation produced a near-optimal image every time thereby reducing the frequency of retakes and thus reducing the total dose to the patient. A variety of attempts to develop electronic means of acquiring digital diagnostic images have been reported with perhaps the most promising involving a scanning linear array of photodiodes and collimation (RadioGraphics, Volume 9, Number 6, November 1989, page 1148). Thus far, such devices have not been adapted for routine clinical use.

Diagnostic fluoroscopic imaging is currently practiced using an x-ray image intensifier tube (RadioGraphics, Volume 9, Number 6, November 1989, pages 1137, 1138). The image intensifier tube converts incident radiation to light, typically using a CsI screen. Then, through a series of steps, an amplification of the light is achieved and the light output from the image-intensifier tube is captured and converted to an electronic image by means of a camera, a CCD, or some similar device. An x-ray image-intensifier tube along with a camera, or a CCD, or some similar device constitutes an x-ray image-intensifier (XRII) fluoroscopic imaging unit. While XRII units are very useful fluoroscopic imaging devices, they suffer from a number of serious deficiencies. First, XRII units are relatively bulky having a length usually exceeding 50 cm. This is a definite hindrance in various clinical procedures. For example, XRII units restrict the possible motions of radiotherapy simulators thereby limiting the treatment positions that can be simulated. Restrictions also occur in a variety of diagnostic x-ray procedures due to the bulk of the XRII unit. Second, the quality of the images are compromised by various well-known effects associated with image intensifiers and cameras which lead to distortions and glare. Furthermore, XRII units are easily affected by stray magnetic fields and are generally difficult to maintain at peak imaging performance. It would be very useful to have an alternative technology, which is thin, light-weight, and free of distortion, glare, and the effects of magnetic fields suffered by XRII units. Furthermore, such an alternative technology would allow for a portable fluoroscopic imager offering high quality images. This possibility is generally not practical with XRII units.

From the above discussion, it is clear that fluoroscopic imaging with both megavoltage X rays and gamma rays and diagnostic quality X rays involves production and presentation of consecutive images during the course of an irradiation. Consequently, such imaging is inherently real-time in nature. Further, radiographic imaging as practiced with technologies such as film-screen systems and photostimulable phosphors requires some time consuming intermediate step (such as film development or laser-scanning) before the image is available for presentation. Such imaging is thus not real-time in nature. A variation of diagnostic radiographic imaging occurs when a series of x-ray films are rapidly exposed, one after the other, or on a continuous roll of film. However, since the images are not available for presentation during, or immediately after, the irradiation, this is also not real-time imaging. However, if a practical technology could be developed which would provide presentation of high quality radiographic images immediately after irradiation, this would then be another form of real-time imaging. Moreover, if this alternative imager offered the images in digital form, this would be of considerable utility as it would facilitate electronic processing and presentation of the images as well as electronic archival and transfer. As outlined above, the existence of a technology offering real-time radiotherapy and/or diagnostic digital imaging would be of definite benefit.

In selecting the materials for a real-time imager for megavoltage photon radiation therapy and diagnostic x-ray imaging, care must be taken that the materials can withstand high levels of radiation exposure over long durations of time. Another consideration is that the radiation detecting elements be arranged over a relatively large surface area. For instance, a detection surface of at least 25×25 cm$^2$ is necessary for head and neck portals in radiation therapy. For pelvic, abdominal and thoracic portals, a surface area of 50×50 cm$^2$ is desirable. For dental imaging, an imager as small as approximately 2×2 cm$^2$ and up to approximately 3×4 cm$^2$ would be clinically useful. For diagnostic radiography and fluoroscopy, imagers as large as 60×60 cm$^2$ would be useful. Though solid state imagers are highly desirable, the manufacture of crystalline semiconductor detectors over such an area is certainly prohibitively expensive.

The development of a-Si:H (hydrogenated amorphous silicon) has resulted in the realization of a highly radiation resistant material which can be utilized over large surface areas at very economical cost. See V. Perez-Mendez, et al., "Signal, Recombination Effects and Noise in Amorphous Silicon Detectors", Nuclear Instrument and Methods in Physics Research A260 (1987); 195–200, Elsevier Science Publishers B.V.; and I.D. French et al., "The Effect of $\gamma$-Irradiation on Amorphous Silicon Field Effect Transistors", Applied Physics A31, 19–22, 1983, Springer-Verlag.

It is now realized that amorphous silicon thin film transistors have applications to large-area electronics, see H. C. Tuan, "Amorphous Silicon Thin Film Transistor and its Application to Large-Area Electronics," Mat. Res. Soc. Symp. Proc. Vol. 33 (1984) Elsevier Science Publishing Company, Inc.

Amorphous silicon ionizing particle detectors made of hydrogenated amorphous silicon are known which can detect the presence, position and amount of high energy ionizing particles see Street et al., U.S. Pat. No. 4,785,186; however, the patent does not teach how a-Si:H photodiodes can be utilized in coordination with other elements to obtain a real-time imaging device.

Rougeot, U.S. Pat. No. 4,799,094, teaches a photosensitive device having an array of p-doped floating grids which connect with a substrate of lightly n-doped hydrogenated amorphous silicon. Since Rougeot uses transistors as light detectors, the quantity of electron-hole pairs generated would appear quite insufficient to realize real-time imaging.

SUMMARY OF THE INVENTION

Accordingly, one object of the present invention is to achieve a pulse-by-pulse monitoring of the centroid of a transmitted megavoltage radiation beam.

Another object is to obtain real-time radiographic or fluoroscopic images of the patient irradiated with a megavoltage beam.

Yet another object is to measure, in real-time, the transmitted dose of the radiation field in order to help insure and verify the correct delivery of the treatment dose to the target region.

Another object is to obtain real-time diagnostic x-ray radiographic images with immediate presentation after the irradiation without the need to wait for film development or laser scanning of a photostimulable phosphor plate.

Another object is to obtain real-time diagnostic x-ray fluoroscopic images with a device far more compact than an image-intensifier fluoroscopic unit and offering higher quality images without the distortion, glare, and effects of magnetic fields suffered by XRII units.

Another object is to obtain real-time diagnostic x-ray fluoroscopic images with an imager considerably thinner than a bulky XRII unit thus resulting in fewer restrictions in radiotherapy simulation and other diagnostic x-ray procedures.

Another object is to obtain real-time diagnostic fluoroscopic and radiographic images with an imager offering the imaging information directly in digital form.

Another object is to obtain real-time diagnostic quality fluoroscopic images with a device sufficiently compact that it can be made into a portable unit.

Another object is to obtain real-time diagnostic quality radiographic images with a portable device that can operate independently of a film processor or laser reader.

These and other objects are achieved by providing a real-time imaging device for use with an incident ionizing radiation such as produced in the form of megavoltage radiation bursts in radiation treatment machines or from a diagnostic X-ray generator, including a conversion layer for converting photons from the incident ionizing radiation into electrons, a phosphor or scintillating layer in which the electrons created in the conversion layer create visible light photons, and an upper electrode layer which is transparent and allows the visible light from the phosphor or scintillating layer to pass through to a plurality of photosensitive sensors arranged in rows and columns to form a radiation detecting surface area. Each photosensitive sensor is paired with a thin film field effect transistor. The RC time constant of pixels on the imaging device is determined by multiplying the resistance of the transistor by the capacitance of the photosensitive sensor and is selected based on predetermined physical and operational parameters discussed hereinafter.

The high energy electrons and visible light photons emitted from the phosphor or scintillating layer and incident upon the sensors constitute an imaging signal. Sufficient amounts of this imaging signal can be detected, creating electron-hole pairs which are stored in the capacitance of the sensors. Thereafter this signal can be read out on a time scale determined by factors discussed hereinafter so that real-time imaging is made possible. Known interfacing electronics consisting of preamplifiers, multiplexors, and digitizers which are connected to the sensor-transistor combinations convert these signals into digital form thereby making this an inherently digital imaging device.

For the application of real-time imaging of a diagnostic x-ray beam, given that the interaction probabilities are considerably higher and the range of the electrons created by the photons much shorter, a single layer for diagnostic-energy photon conversion and creation of the light photons by the resulting electrons suffices.

For both megavoltage imaging and diagnostic x-ray imaging, an alternative is to use sensors made sufficiently thick (50 μm to 2000 μm) that the incident radiation directly interacts with the sensor generating signal in it with no need for either a conversion layer or a phosphor or scintillating layer.

In addition, given the thinness and uniformity of the amorphous silicon sensors and the substrates upon which they are deposited, it is furthermore possible to stack one imager upon another without significant degradation of the imaging information. For example, an array dedicated to determining the position of a scanning radiotherapy beam could be positioned under an array dedicated to imaging the megavoltage photon beam. Alternatively, an array dedicated to real-time diagnostic x-ray imaging could be positioned over an array dedicated to real-time megavoltage imaging. Such positioning would offer tremendous advantages to radiation therapy.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
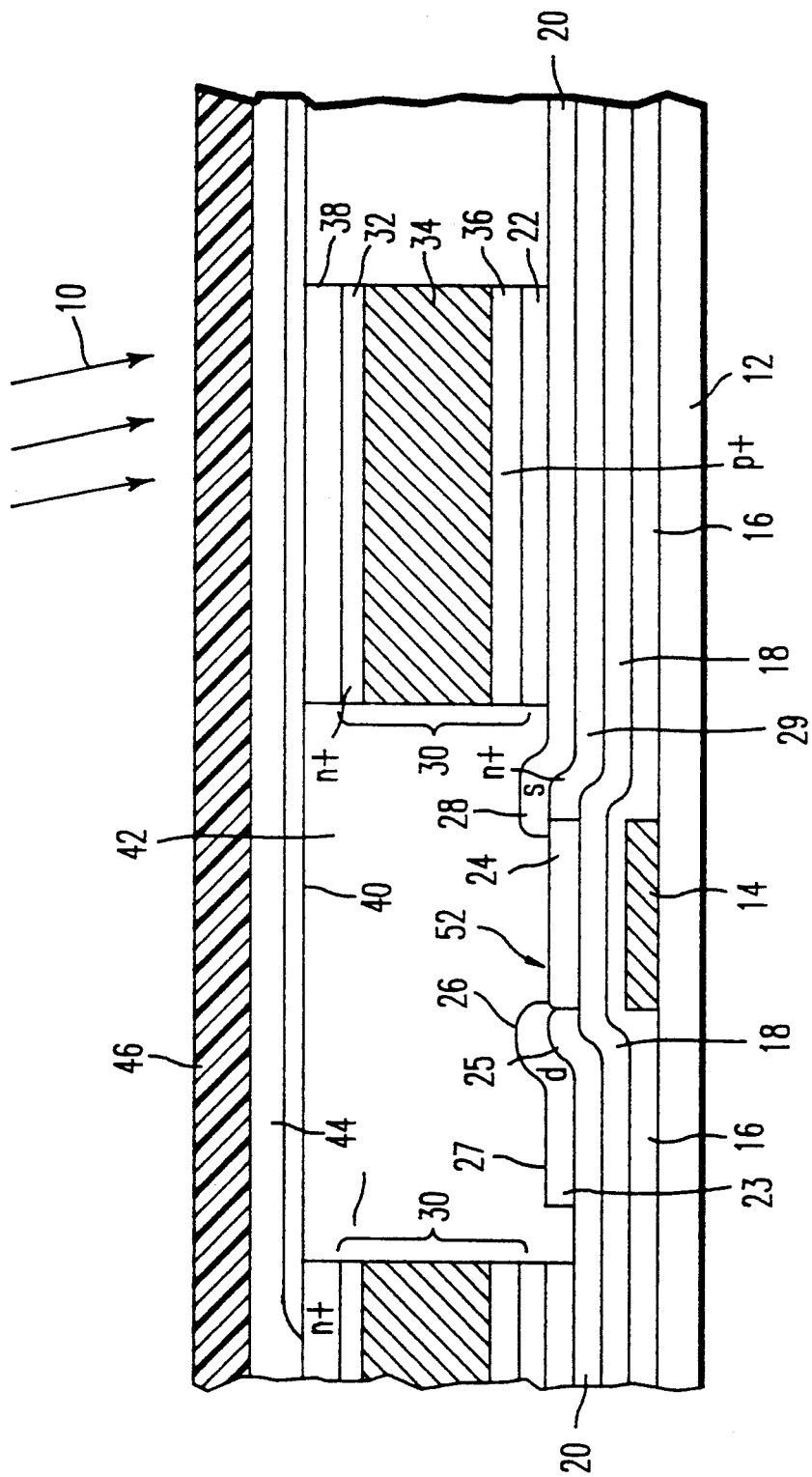
FIG. 1 is a cross-sectional side view of the present invention.

Referring now to the drawings, wherein like reference numerals designate identical or corresponding parts throughout the several views and, more particularly, to FIG. 1 thereof, a sensor 30 and thin-film field effect transistor 52 are shown mounted upon a glass substrate 12. The gate contact region 14 of the thin-film field effect transistor is seen to be positioned atop the glass substrate 12. Surrounding the gate contact region is a gate dielectric layer 16 of silicon nitride $Si_3N_4$ which also makes contact with the glass substrate 12. Above gate dielectric layer 16 is an a-Si:H layer 18.

Directly above the gate contact region 14 and making contact with the a-Si:H layer 18 is a second dielectric layer 24 made of silicon nitride. Adjacent to the sides of the lower portion of the second dielectric layer 24 are located n+ doped drain and source layers 25, 29 which are portions of n+ layer 20 positioned so as to sandwich the lower portions of the second dielectric layer 24 therebetween. A drain contact 26 and a source contact 28 are positioned so as to sandwich the upper portion of the second dielectric layer 24 between them. These structured layers above and to the side of the gate contact region constitute a thin-film field effect transistor 52. Alternatively, polycrystalline silicon thin-film-transistors can be implemented to achieve faster read-out-speed by virtue of its channel mobility which is ~30 times higher than that of a-Si:H.

This thin-film field effect transistor 52 is connected to a sensor 30 which constitutes a p-i-n photodiode. The sensor 30 is connected to the source contact 28 of the thin-film field effect transistor 52 by means of lower electrode layer 22 integrally formed with source contact 28.

Above lower electrode layer 22 is p+ doped a-Si:H layer 36, layer 36 being approximately 400 Å thick. Above layer 36 is an intrinsic a-Si:H layer 34 which is at least 0.1 microns thick and may be up to 3 microns or more thick for reasons which will be subsequently discussed. Above the intrinsic layer 34 is an n+ doped layer 32 of a-Si:H, which is approximately 100 Å thick.

Above n+ doped layer 32 lies the upper electrode 38 which is made of a material transparent to visible light. A material such as indium tin oxide (ITO) is a suitable material for the upper electrode 38. A phosphor or other scintillating layer 44 for purposes of converting electrons to visible light is located directly above and preferably makes contact with the transparent upper electrode 38. Phosphor or scintillating layer 44 may be a calcium tungstate ($CaWO_4$) scintillating screen (e.g. a CRONEX TM screen), a gadolinium oxysulfide ($Gd_2O_2S$:Tb) scintillating screen (e.g. a LANEX TM screen), a CsI scintillating screen, or other suitable material.

A n-i-p sensor is an alternative to the p-i-n sensor shown in FIG. 1. An n-i-p sensor offers somewhat better signal response since the signal derives primarily from electron transport compared to hole transport for the p-i-n sensor. In addition, in an n-i-p sensor, the p layer may be made of materials other than a-Si:H, e.g., microcrystalline silicon or silicon carbide in order to increase the transparency of this layer, thereby increasing the signal size.

For megavoltage beams, a photon-to-electron conversion layer 46 is located directly above and makes contact with a phosphor or scintillating layer 44. Conversion layer 46 may be a 1 millimeter thick copper sheet or a comparable layer of tungsten or lead or other suitable material; however, the thickness can be varied depending on the energy level of the radiation to which it is exposed. A 1 mm thick copper sheet when combined with a CRONEX TM scintillating screen and exposed to a megavoltage (~3 to 50 MV) photon beam produces pulses of light for about 10 microseconds. A 1 mm thick copper sheet when combined with a LANEX TM scintillating screen produces pulses of light for about 1 millisecond when exposed to a megavoltage beam.

Optionally, a suitable phosphor or scintillating layer may be deposited directly onto the sensors or onto the photon-to-electron converter in order to optimize the spatial resolution of the imager. For diagnostic imaging, the interaction of X rays with the scintillation layer 44 is such that the conversion layer 46 is not necessary.

In the case of megavoltage imaging, another option is to position above the array a phosphor or scintillating layer 44 which is sufficiently thick that there is no need for a separate photon-to-electron conversion layer 46. In this case, the incident megavoltage X rays or gamma rays interact in the phosphor or scintillating layer creating high energy electrons which then generate light in the same layer.

In yet another embodiment of the invention, the sensors 30 are made sufficiently thick (50 $\mu$m to 2000 $\mu$m) that there is no need for neither a photon-to-electron conversion layer 46 for megavoltage imaging or for a phosphor or scintillating layer 44 for megavoltage or diagnostic imaging. In this case, the imaging signal originates from direct interaction of the incident radiation with the sensor resulting in the creation of electron-hole pairs which are stored in the capacitance of the sensor. In this embodiment, the resulting spatial resolution of the imager would be improved having eliminated the light creation stage where scattering of light results in an inherent loss of spatial resolution. In this case, the sensors could consist of thick hydrogenated amorphous silicon diodes, non-limiting examples of which are described in Naruse et al, IEEE Transactions On Nuclear Science, Vol. 36, No. 2, April 1989, pp. 1347-1352 and Perez-Mendez et al, Materials Research Society, Vol. 149, 1989, pp. 621-632, or of a thick layer of chalcogenide glass, such as amorphous selenium, $As_2Se_3$, $GeSe_2$ and related alloys, (See U.S. Pat. No. 5,017,989) (replacing the p+ doped a-Si:H layer 36, the intrinsic a-Si:H layer 34, and the n+ doped a-Si:H layer 32), or some other suitable material.

As is shown in FIG. 1, polyimide 42 is placed over the field effect transistor 52 and between sensors 30 to provide planarization and passivation.

Figure 2:
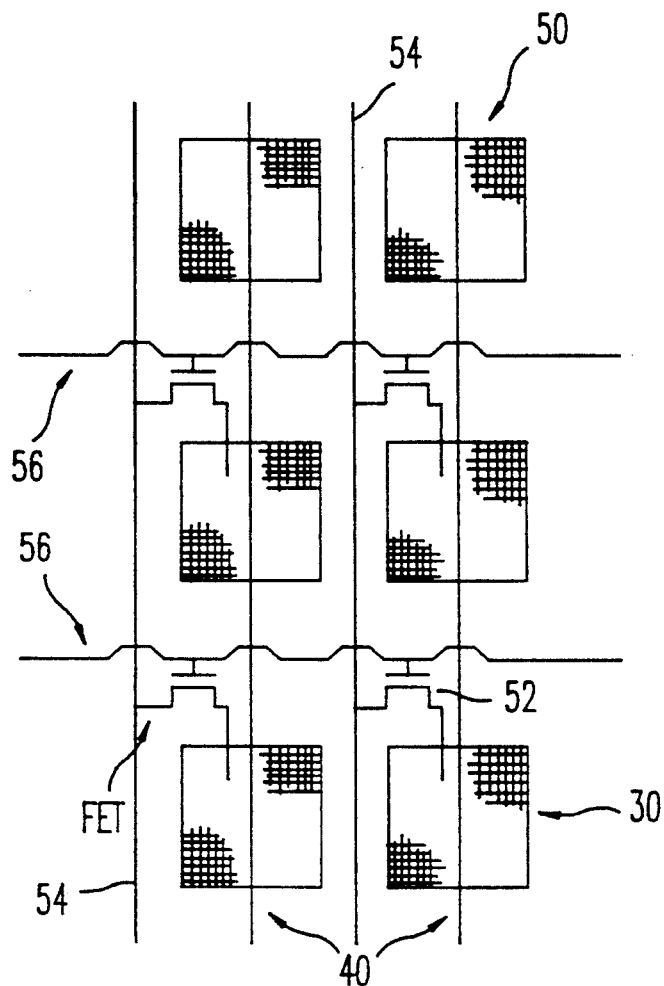
FIG. 2 is a top view illustrating the array of sensors and transistors.

FIG. 2 shows an array of sensors 50 according to the present invention. Biasing lines 40 are seen to connect the sensors 30 by being connected across the upper electrode layer 38, shown in FIG. 1, of each sensor in a given column. As will be appreciated by those skilled in the art, a metal layer (not shown), e.g., of aluminum, is coincident with those regions of biasing lines 40 which are located between the sensors 30. Such a metal layer serves to shield the transistors 52 from light. Signal lines 54 are shown to connect to the drain of each field effect transistor 52 in a given column.

From FIG. 1 it can be seen that a drain electrode layer 23 extends away from a side of drain contact 26. Metallization (not shown) extends vertically upward from the end 27 of the drain electrode layer 23 away from transistor 52. This metallization is constructed to connect with a signal line 54 which lies on the substrate 12 beside sensor 30. Gate select lines 56 (FIG. 2) are seen to connect the gates of the thin-film field effect transistors located in a given row.

Thus, each sensor and its accompanying thin-film field effect transistor constitute an imaging pixel. These pixels are arranged in rows and columns so as to form an array 50 mounted upon glass substrate 12 thereby constituting an imaging panel.

Figure 4:
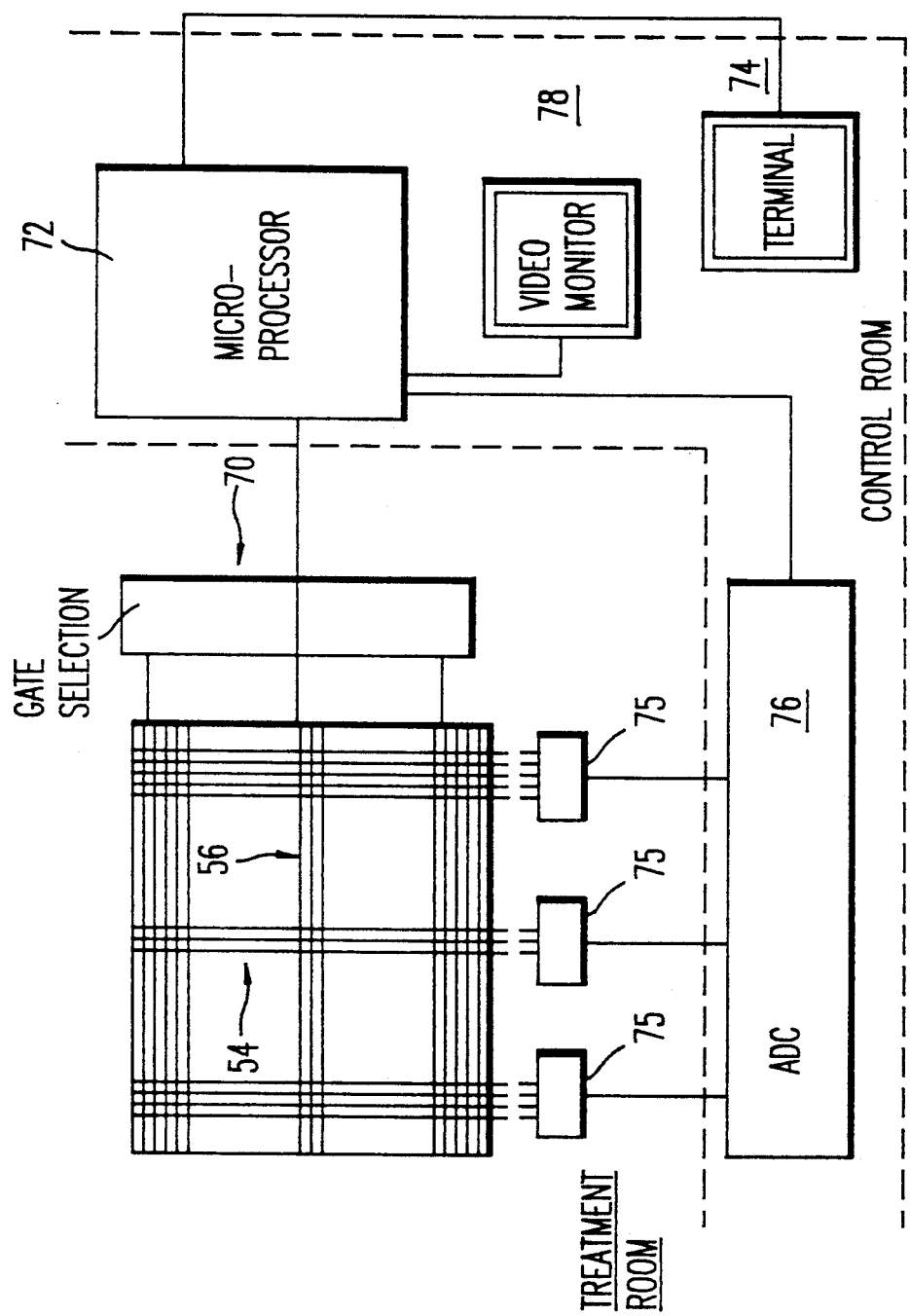
FIG. 4 is a schematic block diagram illustrating interfacing of sensors and transistors with known support electronics.

One example of such an imaging panel is formed as a $25.6 \times 25.6$ cm$^2$ imaging surface made up of approximately 65,536 individual sensors arranged in a $256 \times 256$ array corresponding to a pixel pitch of 1000 $\mu$m. In such an array each sensor is over 0.9 millimeters long with a density of 1 sensor per square millimeter. Four $25.6 \times 25.6$ cm$^2$ panels can be combined to form a roughly $50 \times 50$ cm$^2$ surface so that the invention can be utilized for virtually an imaging function. Due to the thin nature of the substrate on which the imaging array is fabricated, it is possible to configure the imager into a package with a profile of 1-2 cm, about equal to that of a film cassette FIG. 4 shows the layout of the read-out electronics. Each gate select line 56 is addressed sequentially with a shift register. Each of the signal lines 54 is connected to a preamplifier and switching electronics. Either a charge-sensitive or a voltage preamplifier may be used. If it is the latter, then a capacitor is included on the array at each signal line. The signals from a row of pixels are read out by providing a gate pulse to the corresponding gate select line 56 so as to render the thin-film field effect transistors along the gate select line conducting. The charge or the voltage is then sensed for each of the signal lines 54, after which the signal line is reset to ground potential before the next gate pulse.

As shown in FIG. 1, a radiation beam 10 is directed upon the photon-to-electron conversion layer 46 which converts the photons of the radiation beam to electrons, some of whose energy is absorbed in phosphor or scintillating layer 44 and thereby converted to visible light. Alternatively, the conversion layer 46 is not present, and some or all of the photons of the incident radiation beam are converted to electrons in the phosphor or scintillating layer in which they generate visible light. In either case, this visible light passes through the transparent upper electrode 38 and into the sensor 30 where electron-hole pairs are generated in the intrinsic layer 34. The present invention allows up to $\sim 50$ to $\sim 90$ percent of the visible light photons emitted from phosphor or scintillating layer 44 and intercepted by the sensors to be converted to electron-hole pairs. In the case when the sensors are thick (50 $\mu$m to 2000 $\mu$m), following well understood principles the radiation can interact directly with the sensors creating electron-hole pairs to a degree sufficient to make the presence of a photon-to-electron conversion layer and/or a phosphor or scintillating layer unnecessary. The sensors 30 have a capacitive effect when a reverse bias is applied to them by means of the biasing lines 40. This reverse bias causes the electron-hole pairs to be attracted to the upper and lower electrodes 38 and 22 where the signals generated from the radiation bursts are thus stored.

The attenuation of light in a-Si:H is well understood and the thickness of the intrinsic layer needed to completely absorb all incident visible light is a function of wavelength. The thickness of the intrinsic layer 34 may be usefully varied from 0.1 to 3.0 microns or more. This allows a fraction or all of the incident light to be absorbed in the intrinsic layer as shown in "Signal, Noise, and Readout Considerations in the Development of Amorphous Silicon Photodiode Arrays for Radiotherapy and Diagnostic X-ray Imaging", SPIE Vol. 1443 Medical Imaging V: Image Physics (1991) pp 108-119, Antonuk, et al. As the intrinsic layer thickness increases, there are other effects of note. First, the capacitance of the sensors decreases thereby affecting the time constant for readout and reinitialization. Second, the applied bias must increase proportionally in order to ensure that the electron-hole pairs generated throughout the intrinsic layer are efficiently collected and positioned at the upper and lower electrodes. Thus, the choice of intrinsic thickness is governed by various considerations including the wavelength of the light emitted by the phosphor or scintillating layer, how much of the light it is desired to use, and the desired readout speed. In the case of thick (50 μm to 2000 μm) sensors, the choice of thickness will involve considerations of the fraction of the incident radiation it is desired and possible to have interact directly with the thick sensors as well as readout speed.

It should be noted that the present invention will produce real-time images with any form of incident ionizing radiation including electrons, protons, neutrons, deuterons, alpha particles, etc. in addition to gamma rays and X rays. Furthermore, the absorption properties of the sensors can be tailored to utilize light emitted from the phosphor or scintillating layer for wavelengths extending across the visible region and perhaps into the ultraviolet region.

For a given energy, E, of incident visible light, the photons are absorbed with a spatial distribution given by $\exp(-\alpha(E)x)$ where x is the distance from the surface and $\alpha(E)$ is the absorption coefficient for the photon energy E. The sensor material has a particular absorption spectrum $\alpha(E)$, depending on its band gap $E_G$. When a phosphor or scintillating material is deposited on or otherwise positioned over the sensor, it is desirable to match the absorption spectrum of the sensor to the emission properties of the phosphor or scintillating material. The a-Si:H sensor absorption spectrum may be changed by alloying with other elements. The alloy a-$Si_x$:$C_{1-x}$:H, $0<x<1$, has an increased band gap and is suitable for phosphors which emit in the green and blue regions of the spectrum. The alloy a-$Si_y$:$Ge_{1-y}$:H, $0<y<1$, has a reduced band gap and is suitable for phosphors emitting in the red region of the spectrum. It is desirable that the n+ and p+ doped contact layers also have their absorption spectra matched to the emission of the phosphor. In particular the top layer should be as transparent as possible because light absorbed in this layer does not contribute to the measured signal. The a-Si:C:H alloy is suitable for this purpose. In addition a doped microcrystalline silicon film may be used which also has a high transparency.

Each combination of a sensor connected to a thin film field effect transistor (FET) forms one pixel. For the purposes of this discussion, let us regard the pixel as a capacitor, of capacitance $C_S$, in series with a resistor. A given gate select line 56 controls the conductivity of all the FETs along that row. When the gate select lines 56 are at a negative bias, ($\sim -5$ volts), the FET resistance is very high and the transistor is essentially non-conducting. When the gate select lines 56 are at a positive bias, $V_G$, the FETs become conducting with a FET-on resistance of $R_{ON}$. The FET on-resistance, $R_{ON}$, and the sensor capacitance, $C_S$, are given by:

$$1/R_{ON} = (W/L)\mu_{FE}(V_G - V_T)\Gamma \quad (1)$$

$$C_S = \kappa\epsilon_0 A/d \quad (2)$$

where W,L are the width and length in cm, respectively, of the gate of the transistor, $\mu_{FE}$ is the field effect mobility (0.7 to 1.0 cm$^2$/Vsec for a-Si:H), $V_G$, is the gate voltage, $V_T$ is the threshold voltage ($\sim 1$ volt), $\Gamma$ is the gate capacitance per unit area ($\sim 200$ pF/mm$^2 = 2\times 10^{-8}$F/cm$^2$), $\kappa$ is the dielectric constant of a-Si:H ($\sim 12$), $\epsilon_0$ is the permittivity of free space ($8.85\times 10^{-14}$ F/cm), and A and d are the sensor area and thickness in cm.

An external bias voltage, $V_{BIAS}$, is applied to the array of sensors 50 by means of bias lines 40, as shown in FIG. 2, on the array. When the FETs are made conducting, the capacitance of the sensors charges up so that a potential difference approximately equal to $V_{BIAS}$ exists across each sensor capacitance. When the FETs are made non-conducting, leakage current from the sensors slowly discharges the sensors' capacitance. In addition, incident radiation generating light in a phosphor or scintillator placed above the array of sensors 50 also generates a signal in the sensors which discharges the sensors' capacitance. In the case of thick (50 μm to 2000 μm) sensors, the incident radiation generates signal directly in the sensors which also discharges the sensors' capacitance. The greater the intensity of the radiation and the light, the faster this discharging occurs. It should be noted that the FET also has a relatively small leakage current which acts in opposition to this discharging, as is discussed in the publication "Light Response Characteristics of Amorphous Silicon Arrays for Megavoltage and Diagnostic Imaging", Materials Research Society Symposium Proceedings, vol. 219, 1991, pp 531-536, and "The Dynamic Response of Hydrogenated Amorphous Silicon Imaging Pixels", Materials Research Society Symposium Proceedings, vol. 219, pp 173-178, which are hereby incorporated by reference. Thus, the degree to which the sensor capacitance is discharged depends upon the imaging information stored in the pixel (i.e., the amount of light signal) as well as the cumulative effect of the sensor and FET leakage currents.

The act of measuring this stored imaging information also reinitializes the pixel. By making the FETs along a single row conducting, current along each signal line recharges the capacitance of the sensors and thus reinitializes the corresponding pixels. This current is integrated in a charge-sensitive preamplifier (not shown) connected to each signal line. Alternatively, the voltage is sampled by a voltage preamplifier connected to each signal line. Further interfacing electronics produce a digital value which is a measure of the imaging signal read from each pixel. In addition, when the FET voltage is switched from negative to positive to make the FETs conducting, a transient signal, originating from the gate-source capacitance of the FET and the finite resistance of the gate select line, is created. A similar transient of opposite polarity is generated when the FET is switched from positive to negative. Whether the digitized values include these transients is a matter of choice in the design of the electronics and sampling technique. One may choose to include the initial switching transient in order to avoid losing any useful signal. Including the second switching transient has the possible advantage of canceling out the effect of the first switching transient.

The reinitialization of the pixels during readout follows an exponential behavior with a time constant, "$\tau$". The exact value of $\tau$ depends upon the details of the array construction as well as the manner in which the readout is performed. In a simple model of the pixels, $\tau$ is given by the product of the transistor on-resistance, $R_{ON}$ in ohms, times the sensor capacitance, $C_S$ in farads:

$$\tau_{RC} = C_S \times R_{ON} \quad (3a)$$

where $\tau_{RC}$ is the RC time constant of a pixel in this model. In a more complex model, the reinitialization behavior of the pixels is also governed by the finite time required for the switching transients mentioned above. Even if the external gate selection circuitry provides an instantaneous voltage step, the finite gate-source capacitance of the FET and the finite resistance of the gate select line will insure that the voltage change applied to the transistor gates will not be instantaneous. Moreover, this transient settling time will increase as the arrays, and thus the resistance of the gate select lines, becomes larger. While the contribution of these switching transients to the reinitialization behavior can be large in some cases, it is highly desirable to make it negligible. This can be accomplished through the use of low resistance metal, e.g., Al, for the gate select lines 56. In this case, the aforementioned simple model which predicts a reinitialization behavior with a time constant, $\tau$, given by $\tau_{RC}$, will be reasonably accurate in all cases.

In our capacitor-resistor model for the pixels, the recharging of the sensor capacitance would follow an exponential behavior with a time constant, $\tau=\tau_{RC}$, where $\tau_{RC}$ is given by the product of the FET on-resistance, $R_{ON}$, times the sensor capacitance, $C_S$. In this simple model with $\tau=\tau_{RC}$, the recharging, $Q(t)$, of the sensor capacitance back to its initial charge, $Q_{PIXEL}$, is described by a simple exponential:

$$Q(t) = Q_{PIXEL}(1 - exp[-t/\tau_{RC}]) \qquad (3b)$$

The inventors have made a systematic study of the reinitialization behavior of pixels and the results have been submitted for publication to the 1991 IEEE Nuclear Science Symposium and Medical Imaging Conference, in an article entitled "Radiation Response Characteristics Of Amorphous Silicon Arrays For Megavoltage Radiotherapy Imaging", which article is hereby incorporated by reference.

In this paper, measurements of the reinitialization time constant, $\tau$, have been reported for a variety of arrays. An example of the reinitialization behavior is shown in FIG. 1 of the paper. Such reinitialization data are found to be well described by an exponential function of the form given by Equation (3b). Such a function is fit to the data and the time constant used in the fit, $\tau$, is allowed to be a free parameter determined by the fit. The resulting values of $\tau$ are given in Table III of the paper along with the ratio of $\tau$ to the calculated values, $\tau_{RC}$. In the case of the 450 μm arrays, the measured time constants, $\tau$, are in close agreement with the calculated value, $\tau_{RC}$. While $\tau_{RC}$ is less than $\tau$ for the 270 μm and 900 μm arrays, this is probably due to the fact that the 270 μm and 900 μm arrays are of a first-generation design, while the 450 μm arrays are of a newer design. The 450 μm arrays, which were specifically designed for the radiotherapy application, are representative of the practical imaging devices that are being developed. In addition, it is interesting to note that the measured time constants for the 450 μm arrays are well under 10 μs, a feature that was designed into these arrays by choosing a W/L ratio of 16:1 (see Table I of the paper).

These results demonstrate that the calculated value of the reinitialization time constant, $\tau_{RC}$, is in reasonable agreement with the measured time constant, $\tau$.

In general, it is highly desirable to design the arrays so that the time constant $\tau$ is as small as possible since the contribution of noise to the signal, measured by the interfacing electronics located off of the array, will be minimized when the sampling of the imaging signal content of the pixels is as brief as possible. There are additional considerations which set a limit on the maximum value that the time constant, $\tau$, may have. These considerations concern the time to read out, i.e. sample and reinitialize, a row of pixels. The specification of a readout time implies a maximum value for the time constant, $\tau$. The shorter the time constant, $\tau$, the faster the pixels can be sampled and reinitialized and thus the faster the rows can be read out. Faster row readout, in turn, can be used to allow image frames to be produced more quickly. It is of interest to examine factors which place a requirement on readout time.

A first factor (1) pertinent to required read out time is that the pixels should be reinitialized to a degree consistent with the needs of the imaging application. Specifically, if the application requires a contrast sensitivity of X% for a given signal size, the array must be operated so as to provide a signal-to-noise sufficient to allow an observer to perceive this contrast. A rule of thumb is that the signal-to-noise should be about 3 to 4 times better than the desired contrast sensitivity. For example, a contrast sensitivity of 0.3% is 3 parts in 1000 and thus requires a signal-to-noise of at least 1000 to 1. The pixels should be reinitialized to a degree consistent with the required signal-to-noise so as to prevent the carry-over of signal into the next frame. Thus, during readout, the FETs should be left conducting sufficiently long to achieve this. In the above example, this means that the sensors should be reinitialized to at least 1 part in 1000.

A second factor (2) regarding readout time is the requirement that the imaging signal content of the pixels be sampled to a degree consistent with the needs of the imaging application. As is the case of factor (1), the FETs should be left conducting sufficiently long to achieve this. However, whether voltage or charge is being sampled, this duration will, at most, be equal to, and often, be less than that needed to satisfy factor (1).

A third factor (3) regarding readout time is the requirement for a certain speed of presentation of images as set by the application. In fluoroscopic imaging, an application will demand a certain number of frames per second. In real-time radiographic imaging, an application will demand that the image be available for presentation within a specified time after the irradiation. Moreover, because the pixels drift toward saturation whenever the FETs are nonconducting, it is highly desirable to quickly readout the array after the termination of the irradiation in radiographic imaging so as to preserve image quality.

A fourth factor (4) regarding readout time concerns the many effects associated with the interfacing electronics which contribute to the minimum time required to read out a single row. For example, after the gate select line has been returned to a negative bias voltage, the feed-back capacitor on the preamplifier must be reset before the next row of pixels can be read out. In practice, this will be a small and negligible effect. Moreover, in principle, the interfacing electronics can be constructed so that only factors (1), (2), and (3) define the required readout time.

Thus, the time required to read out a single row will be dominated by the requirement that the pixels be reinitialized and sampled to a degree consistent with the needs of the imaging application, factors (1) and (2), and by the requirement for a certain speed of presentation of images as set by the application, factor (3). The readout time requirements thereby imposed may be achieved by constructing and operating the array so that the reinitialization time constant, $\tau$, is sufficiently short. The limitation imposed on $\tau$ by factors (1), (2) and (3) may be quantified as follows.

In order to reinitialize the pixel to a degree consistent with the contrast sensitivity needs of the imaging application, the FETs on a row should be left conducting for a sufficient number of time constants, $N_\tau$, so as to be consistent with the required signal-to-noise, SN. Thus:

$$1/SN = \exp(-N_\tau) \qquad (4a)$$

or $$\ln(SN) = N_\tau \qquad (4b)$$

In the previous example, a signal-to-noise of 1000:1, i.e., SN=1000, would require that $N_\tau = \sim 7$.

During imaging, the pixels integrate an incident radiation-generated signal and are read out, one row at a time, to measure this signal. A single image, or frame, results when such data has been acquired for all or some fraction of the pixels. There are numerous manners of operating the array to acquire images. Perhaps the most direct is to read out each row of pixels consecutively, one row immediately after another. However, any order of rows, and even omitting rows, is possible. Moreover, the interval between the readout of rows may be quite different from one scheme to another. Mostly generally, two readout modes may be defined and are described below. In the following discussion, we shall assume that all rows are read out in order starting from the first row but we recognize that alternative readout schemes are possible.

In a "fluoroscopic" mode, the radiation is continually on and images are acquired consecutively, one image frame after another without pause. Such a mode of operation allows motion in the object imaged to be observed in real time, e.g. the rhythmic beating of the heart. In this mode, it is desirable that imaging information from one frame not carry over into the next frame. A straightforward manner of accomplishing this is to insure, for the readout of each row of pixels, that the sensors are reinitialized to a degree consistent with the desired signal-to-noise to be achieved in the radiation image, as set forth in Equations (4a) and (4b). It is also necessary to achieve the number of frames per second demanded by the imaging application.

Figure 6:
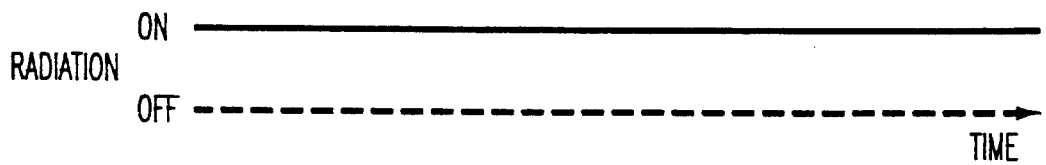
FIGS. 6 and 7 are timing charts illustrating various manners of operation of the present invention.
Figure 6:
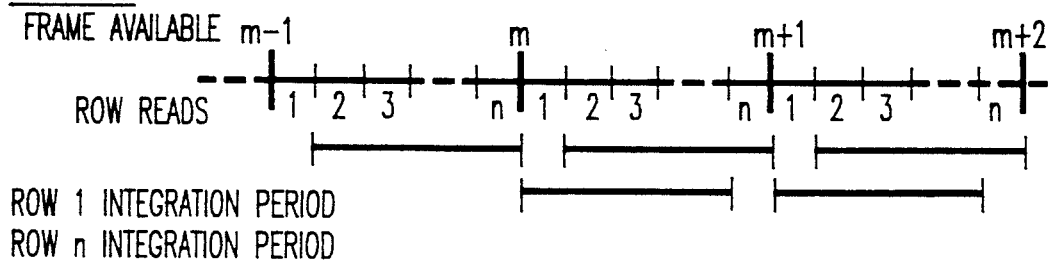
Figure 6:
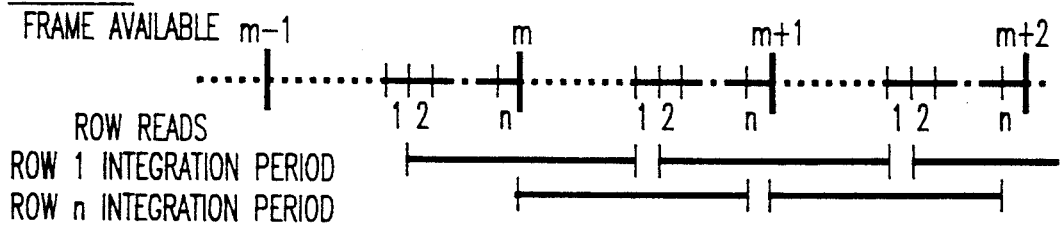
Figure 6:
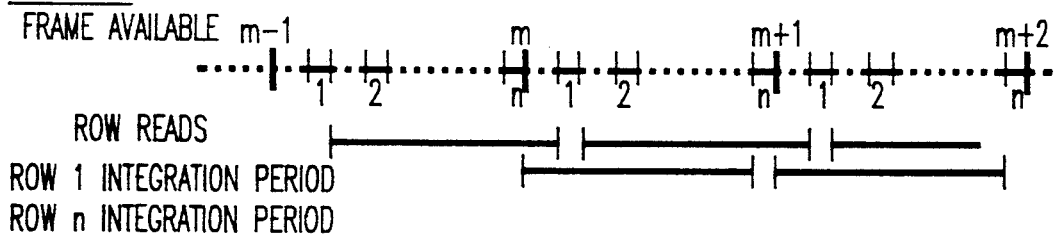
Figure 6:
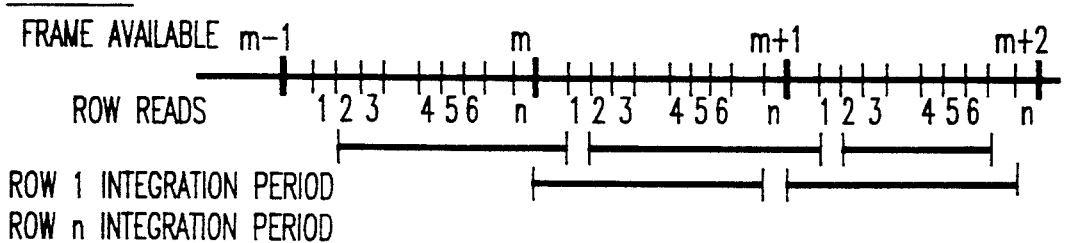

FIG. 6 schematically illustrates four examples of timing schemes for row readout for the fluoroscopic mode. In each case, the time at which the data for the most recent frame is available is marked ("M−1", "M", "M+1", "M+2" . . . ). Also, the time interval during which each row is read is illustrated ("1", "2", . . . "n"). Finally, the duration of the integration interval for the first row (row "1") and the last row (row "n") is shown. The four examples are as follows. In F-MODE-A the rows are read out, one immediately after the other without pause. Then, with no pause, readout begins again. In F-MODE-B the rows are read out, one immediately after the other, until the whole array is read. There is then a pause before readout resumes. In F-MODE-C the rows are read out at a steady pace with a pause between each row. IN F-MODE-D, a small group of rows is read out, one immediately after the other, followed by a pause, followed by the readout of another small group. In the case shown, the numbers of rows in a group is 3 but any number is possible. These four examples generally describe most manners of reading out the array in a regular fashion. However, the inventors recognize that alternative manners of fluoroscopic mode readout exist.

In a "radiographic" mode, the radiation is present for a finite period, $t_R$, which may be preselected. A single image is acquired by allowing the array of sensors 50 to integrate over this period and then reading out the information immediately after the termination of the radiation. It is desirable that the array of sensors 50 be initialized immediately before the commencement of the radiation to a degree consistent with the signal-to-noise needs of the application, as set forth in Equations (4a) and (4b). It is desirable for this mode that the imager and the control of the radiation source be coupled so as to insure that the array of sensors 50 was correctly initialized before the beginning of the $t_R$ period. Moreover, this would insure that no radiation would be "wasted" (i.e., unused).

Figure 7:
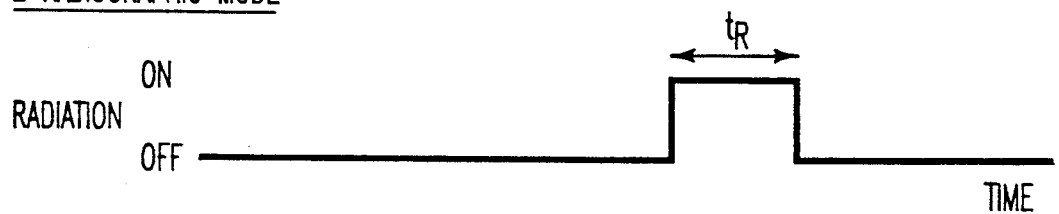
Figure 7:
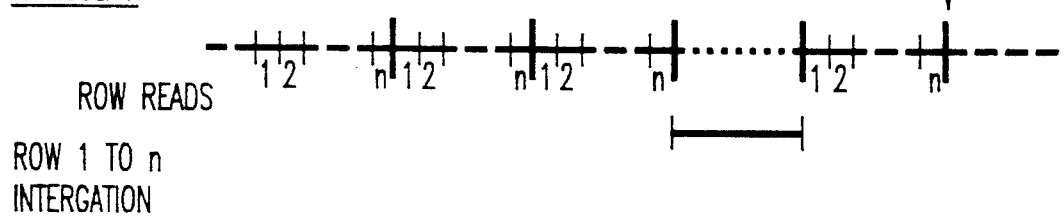
Figure 7:
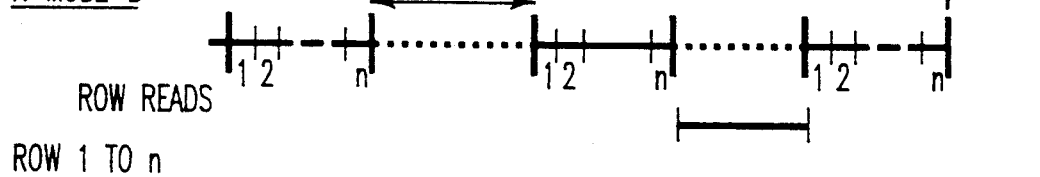
Figure 7:
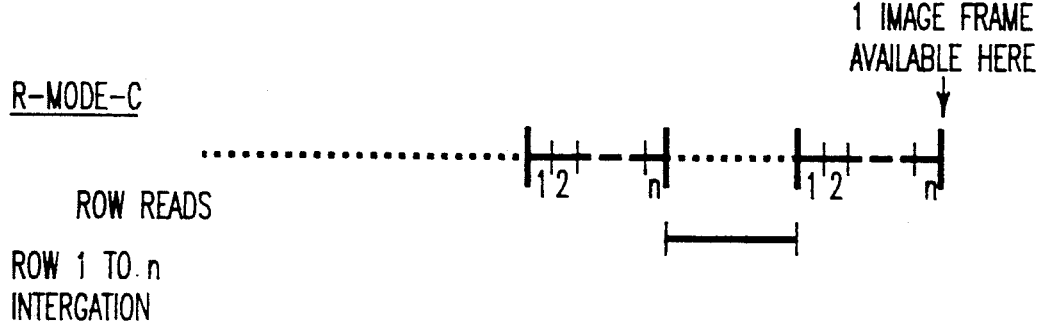

There are many possible manners of initializing the array of sensors 50 prior to the irradiation period. Three examples of perhaps the most useful ways are shown in FIG. 7. In R-MODE-A the array is being continually read out, one row after the other without pause other than during the irradiation. This manner has the merit that the integration period can begin as soon as the row currently being read out is completed, wherever on the array this is since there is no advantage to doing otherwise. Thus, the delay between the request for radiation and the actual beginning of radiation is an absolute minimum in this case. In R-MODE-B, the array is being read out, one row after the other without pause between the rows, but with a pause of duration $t_1$ between the completion of one readout of the array and the beginning of the next. This duration could be anything, and in particular equal to $t_R$, in the event that $t_R$ were predetermined. This manner might offer advantages for calibration purposes. In R-MODE-C, unlike any other manner thus far mentioned, the array is not being continually read out. Rather, upon the receipt of a signal indicating that an irradiation is to begin, the rows are readout one after the other until the entire array is initialized and then the irradiation begins.

In radiographic mode, it is also desirable that the array be read out sufficiently fast so as to allow the presentation of the image within a specified time after the irradiation a well as to insure that the image quality does not deteriorate due to drift of the pixels.

The capacitance of each sensor and the resistance of each transistor should be designed so that the product of their respective capacitances and resistances is less than or equal to the time constant necessary to satisfy the required single row readout time. With the signal information stored in the pixels adequately sampled, the pixels adequately reinitialized, and the images presented at the required speed, real time imaging is made possible.

The intrinsic layer 34 must be at least 0.1 microns thick or greater for purposes of converting and collecting photons over virtually the entire visible spectrum. As the intrinsic layer increases in thickness, the direct ionization signal from high energy quanta increases, and the sensor capacitance diminishes. If the sensor is made sufficiently thick (50 $\mu$m to 2000 $\mu$m), the imaging signal may derive entirely from the direct interaction of incident radiation with the sensor with no need for an photon-to-electron conversion layer and/or a phosphor or scintillating layer to create visible light photons.

Furthermore, as the aspect ratio (W/L) of the thin-film field effect transistor is increased, resistance is reduced. Thus, by widening the channel of the field effect transistor, an increase in the aspect ratio and consequently a decrease in resistance will be realized. Also, resistance can be reduced by increasing the bias received by the gate of the field effect transistor.

Once the signal is stored in the sensors, obtaining a measure of the signal is relatively easy.

Figure 3:
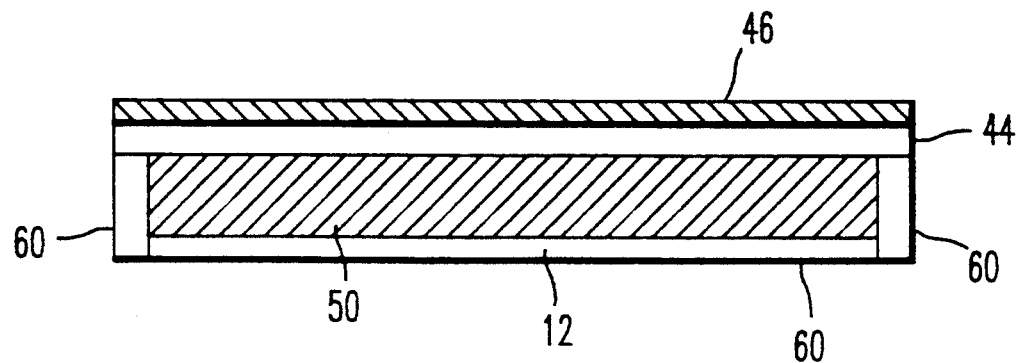
FIG. 3 is a cut away perspective side view of the sensor array enclosed in a shielded housing.

By applying a biasing voltage to the gate select lines the signal stored due to the capacitance of the sensor 30 is released from the source region to the drain region of the field effect transistor and is channeled through the signal lines 54 and on to interfacing electronics As it is essential that the arrays and their electronics be adequately shielded from stray electromagnetic radiation, including visible, radio frequency, and ionizing, FIG. 3 shows a shielded housing 60 made of copper in which an imaging panel 50 is enclosed. In the case of megavoltage imaging, the top of the shielded housing 60 is seen to comprise the photon to electron conversion layer 46 and a phosphor or scintillating layer 44. In the case of diagnostic x-ray imaging, the top shielded housing may either be some thin opaque material, e.q. aluminum, cardboard, etc., or the backside of the scintillator itself. In the case where it is desirable to combine several such imagers, such as one for megavoltage imaging and another for burst-by-burst determination of the centroid of a scanning beam, the arrays for these imagers would be stacked inside of the shielded housing along with their photon-electron converters and scintillating screens.

FIG. 4 shows the array with known interfacing electronics. FIG. 4 serves to demonstrate how the gate select lines 56 can be activated by means of gate select electronics 70 connected to a microprocessor 72 which is connected to terminal 74. The signal lines 54 are seen to be interfaced with preamplification circuits 75 and analog to digital converters 76 which are connected to microprocessor (or imaging workstation) 72 and video monitor 78.

Figure 5:
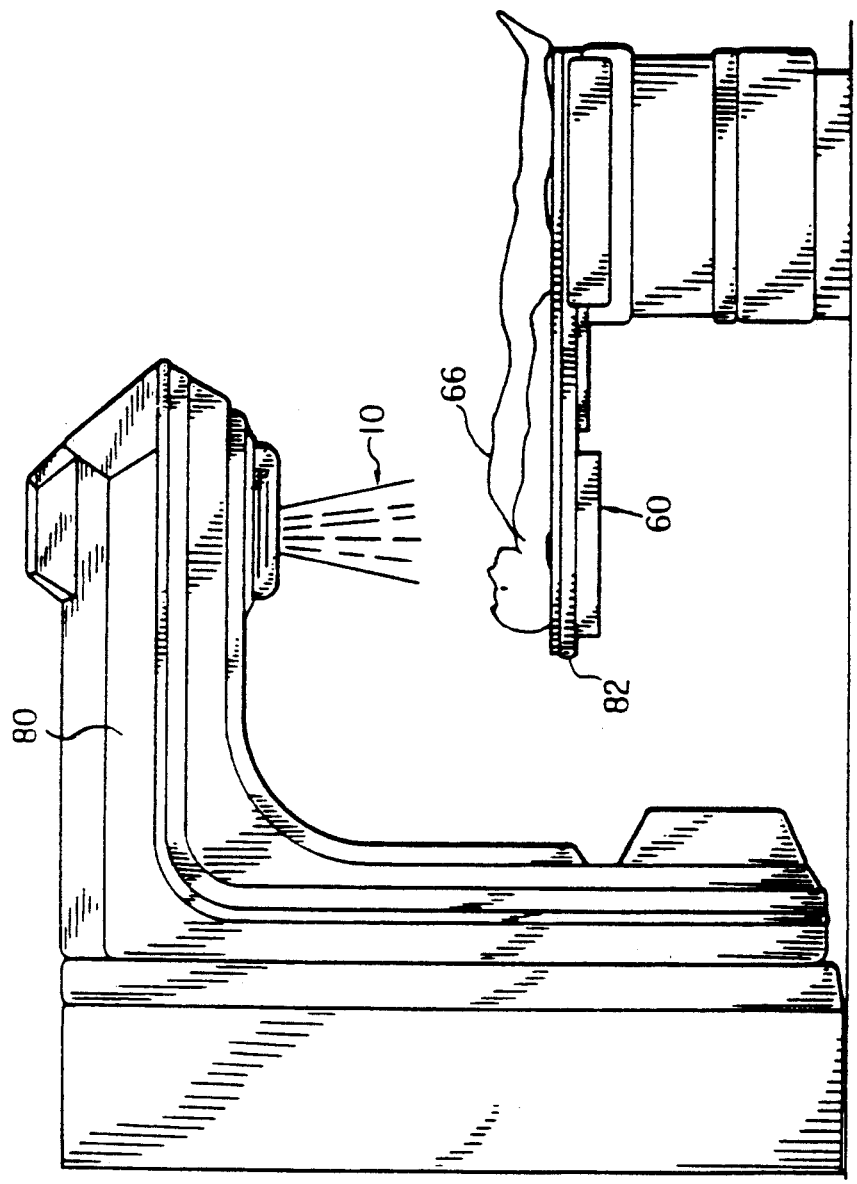
FIG. 5 is a general illustration showing how the present invention is utilized in a clinical setting.

FIG. 5 shows a radiation machine 80 and a patient 66 lying on table 82 receiving treatment from the radiation beam 10. The shielded housing 60 enclosing the array of sensors 50 is seen to lie below the patient underneath table 82. The arrangement would be similar in the case of a diagnostic imager located in a radiotherapy simulator room or in a diagnostic x-ray room.

The discussion which follows is intended to explain what the term "real-time" means in regard to the present invention for both radiographic and fluoroscopic modes of operation as well as centroid determination of a scanning radiotherapy beam.

If the invention is to be used for determining the centroid of a scanning megavoltage beam on a pulse-by-pulse basis then real-time operation requires that a very large fraction, preferably all, of the sensors be read out between bursts. This mode of operation is desirable with a scanning megavoltage beam machine. Such a machine typically has a variable pulse repetition rate ranging from 60 to 500 hertz. Thus, there are 2 to 16.7 milliseconds between bursts. The speed at which a given row from the array must be read out to satisfy this real-time requirement will depend upon the number of rows per array and the pulse repetition rate. Note that this manner of reading out the array is essentially a fluoroscopic mode.

In on form of real-time megavoltage imaging with the invention, it is desired to produce a single image using a given amount of radiation and to view the image immediately at the end of the irradiation. This is real-time radiographic imaging. In one case, it is desired to give the patient a small amount of radiation prior to the main treatment in order to verify the correct position of the beam with respect to the patient. In this case, the signals stored in the sensors would be allowed to accumulate until the termination of the irradiation, at which time the sensors would be read out. The state of knowledge of the megavoltage beams indicates that acceptable images should be possible with the invention after periods of 0.1 seconds to several seconds depending upon the imaging situation and desired contrast. In a second case, all of the entire treatment dose is used to acquire a single image and the image is viewed immediately after the irradiation. This is also a radiographic mode of operation. For either of these cases, real-time imaging would certainly be achieved if the final picture were available within several seconds or less after irradiation.

In another form of real-time megavoltage imaging, it is desirable to produce images, one after the other, during the course of a treatment. This is a fluoroscopic mode of operation. Given that the treatment may last ~10 to 100 seconds or longer and given that there is imaging information after 0.1 seconds to several seconds, real-time operation in this case demands that the imager be read out as quickly as possible after sufficient information has accumulated in the sensors.

In the case of diagnostic x-ray imaging, as in localization imaging, the goal is to produce a high quality image with a minimum of radiation. The present invention allows images to be produced in real-time both for fluoroscopic and radiographic modes of operation whether the radiation is megavoltage or diagnostic x-ray.

With regards to the RC time constant, the invention has been designed so that the rows of sensors can be read out as quickly as possible. This is a consequence of the fact that the external electronics which sample the signals from the sensors also sample noise from various sources, and this noise contribution increases with increasing sampling periods. Hence, it is highly desirable to keep this noise to a minimum by reducing the period during which the charge on the sensors is sampled. As has been mentioned, a major determinant of the speed at which this sampling can occur is given by the capacitance of the sensor times the on-resistance of the thin-film-transistor. Thus, by keeping the RC time constant to a minimum, the present invention achieves real-time imaging with a superior signal-to-noise ratio.

For a given imaging application, a limitation is placed upon the maximum value that the time constant for the pixels, $\tau$, may have. This maximum value is related to the following parameters:

$N_T$ = number of RC time constants taken to sample and reinitialize a given pixel, or equivalently, a row of pixels on an array.

L = length of one column of pixels on the array in cm. L divided by P equals the number of rows of the array when L and P have the same units.

P = pixel-to-pixel pitch - the distance between centers of adjacent pixels on the array in $\mu$m.

IFPS = the instantaneous frames per second, i.e., the effective rate at which the array is being read out. This is given by the inverse of the sum of the times required to read out all the rows of the array. In fluoroscopic mode, FIG. 6, IFPS will be the same as the rate at which images are produced for F-MODE-A. In other modes such as F-MODE-B and F-MODE-C, IFPS will be faster than the rate at which images are being produced due to pauses built into the readout sequence when no rows are being read out. In radiographic mode, IFPS is taken to be $\sim 1.0$ second$^{-1}$ ($= 1$ FPS) for reasons explained later.

SN = the inverse of the degree to which the pixels need to be reinitialized so as to be consistent with the signal-to-noise requirement of the application. For example, if a signal-to-noise of 1000:1 is required by the application, then the pixels need to be reinitialized to at least 1 part in 1000 and thus SN = 1000.

Thus, if one has an array with a column length of L in cm and a pixel pitch of P in $\mu$m and if it is desired to have an instantaneous read out rate of IFPS frames per second, then the time available for sampling and recharging each row is given by:

$$\begin{aligned} TPR &= \text{the time (in micro-seconds) for sampling and recharging a single row} \\ &= 100 \cdot P/(L \cdot IFPS) \end{aligned}$$

The relationship between a desired signal-to-noise, SN, and the number of time constants necessary to achieve this signal-to-noise is given by:

$$1/SN = \exp(-N_\tau)$$

or equivalently $$\ln(SN) = N_\tau$$

If the pixels are to be reinitialized so as to be consistent with the desired signal-to-noise, SN, then the product of the time constant, $\tau$, times the number of time constants, $n_\tau$, required to achieve the desired signal-to-noise must not be greater than the time for reinitializing a single row, TPR:

$$\tau \times N_\tau \leq TPR$$

Thus, this last equation allows one to derive the maximum value for the time constant given an array of column length L (in cm), pixel pitch P (in $\mu$m), and an instantaneous frame rate of IFPS (in fps) and signal-to-noise of SN:

$$\tau \leq TPR/N_\tau$$

$$\leq 100 \cdot P/(L \cdot IFPS \cdot \ln(SN))$$

where the units of $\tau$ are microseconds, i.e., the time constant must obey the condition:

$$\tau \leq \frac{100 \cdot P}{L \cdot IFPS \cdot \ln(SN)} \text{ units of microseconds.} \quad (5)$$

Thus, given this constraint upon the reinitialization time constant, $\tau$, one must design the array so that $\tau_{RC}$ meets the required value of $\tau$.

With respect to the sensors and FETs, a reasonable range of values of the parameters defining the RC time constant $\tau$ is:

- for the sensor thickness, d, from $\sim 0.1$ $\mu$m to $\sim 3$ $\mu$m for photosensitive sensors or in the case of thick sensors which detect the radiation directly without the need for the generation of light, sensor thickness, d, from $\sim 50$ $\mu$m to $\sim 2000$ $\mu$m

- for the sensor area, this will be governed by the pitch. For the current design rules governing array construction, the sensor areas for the 270, 450 and 900 $\mu$m arrays are given in Table I of "Radiation Response Characteristics of Amorphous Silicon Arrays for Megavoltage Radiotherapy Imaging", submitted for publication to the 1991 IEEE Nuclear Science Symposium and Medical Imaging Conference, Antonuk et al. As the pitch decreases, the fraction of the area of the array occupied by the sensors (called the "fill factor") decreases, as approximately shown in FIG. 3 of Antonuk et al, SPIE vol. 1443, Medical Imaging V: Imaging Physics 108–119 (1991). For the arrays of the 3 existing pitches, 270, 450, and 900 $\mu$m, these fill factors are 0.48, 0.62, and 0.83 respectively. Moreover, as the design rules evolve, the fill factors increase allowing progressively finer pitches extending down to perhaps $\sim 25$ $\mu$m. One example of such a design rule change would be to construct the array so that each thin-film transistor is below its associated sensor thereby allowing the sensor to occupy more area thereby increasing the fill factor, a non-limiting example of which is described in Perez-Mendez et al, M.R.S., vol. 149, 1989, pp. 621–632. Such a design change would in turn allow the p+ doped a-Si:H layer 36, the intrinsic a-Si:H layer 34, the n+ doped a-Si:H layer 32, and the upper electrode layer 38 to be continuous and non-pixelated thus occupying the entire surface of the array. In this case, only the lower electrode layer 22 is pixelated thus defining the individual sensors. This would result in the fill factor achieving its maximum value of 1. Biasing lines 40 would no longer be necessary as the upper electrode layer 38 could be connected to an external voltage bias directly. In the case of amorphous selenium sensors, the p+ doped a-Si:H layer 36, the intrinsic a-Si:H layer 34, and the n+ doped a-Si:H layer 32 would be replaced by a continuous thick layer of amorphous selenium. Again, the upper electrode layer 38 would be continuous while the lower electrode layer 22 would be pixelated.

- for the width and length, W and L, of the gate of the transistor, these may be made as long as required while the shortest dimension presently used is $\sim 15$ $\mu$m. This minimum distance could be reduced further to $\sim 8$ $\mu$m.

Ranges for the parameters involved in the determination of time constant by means of equation (5) are presented below for a variety of megavoltage and diagnostic imaging applications. A number of examples of the maximum value of the time constant, $\tau$, as calculated by means of equation (5) are also given. While this list of examples is by no means exhaustive, these calculations demonstrate that the calculated values for the maximum time constant, $\tau$, are quite within the capabilities of the invention, over a wide variety of imaging conditions.

In the following examples, the relationship between the value of IFPS used in the calculations to the imaging conditions is as follows. By far, the most straightforward and convenient manner of operating the array is in a cyclic manner wherein the pattern of recharging of the rows is exactly repeated, cycle after cycle. A variety of such manners for both radiographic and fluoroscopic imaging are illustrated in FIGS. 6 and 7. For fluoroscopy, continual recharging of each row of pixels, one row immediately after the other without pause, is one of the simplest manners and is illustrated as F-Mode-A in FIG. 6. In this case, IFPS is simply equal to the rate at which images are being produced, i.e. the frame rate, and this is the manner of operating the array assumed in the following fluoroscopic examples. For other alternative manners of fluoroscopic operation such as those shown in FIG. 6, the value of IFPS is simply determined once the various timings are specified. For radiography, recharging each row, one immediately after the other, with a pause in this sequence during the irradiation to allow signal integration in the pixels is a straightforward manner of initializing the array before the irradiation and reading out the imaging information after the irradiation. This is illustrated in examples R-Mode-A, R-Mode-B, and R-Mode-C in FIG. 7. For real-time radiography, it is desirable to present an image within several seconds after the irradiation. Since time is required by the interfacing electronics and the imaging workstation, it is a reasonable goal to read out the entire array in ~1 second after the irradiation. This is also sufficiently fast that the effect of post-irradiation pixel drift upon the image quality will be relatively small. In the following radiographic examples, it is assumed that the readout rate is identical before and after the irradiation. In this case, the value of IFPS appropriate for calculations in Equation (5) is 1 fps for radiographic mode. For a different readout speed and/or alternative manners of radiographic operation, the value for IFPS is again determined once the various timings are specified.

For all of the examples of time constant calculations given below, it should be understood that these are the "maximum" values that would allow the readout conditions described. They are based solely on the idea that the sampling and reinitialization times and the speed of image presentation are the only factors contributing to the required speed of the readout of the rows. Other effects such as those previously described and practical problems that one encounters in the electronics would make it prudent to design the arrays so to provide values for $\tau$ approximately one-half of these calculated limiting values. Again, it is well within the capabilities of the invention to satisfy this more stringent requirement For radiotherapy:
- for real-time imaging of the megavoltage beam
  - the pitch, P, will range from ~400 μm to ~1,500 μm
  - the length of a side of the sensitive region of the array, L, will range from ~20 cm to ~60 cm;
  - in fluoroscopic mode, the frame rate will range from 10 frames per second to ~1 frame every 10 seconds. In radiographic mode, the irradiation period for an image will range from ~0.10 seconds to as long as ~100 seconds. However, in radiographic mode at the end of an irradiation integration period, it is desirable to actually perform the readout of the array in ~1.0 second. This is sufficiently fast that, along with the time required by the interfacing electronics and imaging workstation, the image may be presented within several seconds of the irradiation. In fluoroscopic imaging, IFPS is equal to the actual frame rate while in radiographic imaging, IFPS is equal to ~1.0 fps.
- SN will range from ~10 to ~10,000;
- Consequently, some limiting cases for the time constant are:
  - For a high resolution, very large array, operated at a high frame rate, with a reasonably high signal-to-noise, corresponding to P=400 μm, L=50 cm, IFPS=10 fps, SN=1,000, such as used for fluoroscopic megavoltage imaging, $$\tau \lesssim \sim 12 \ \mu s$$

- For a low resolution, medium size array, operated in radiographic mode, with a reasonably high signal-to-noise, corresponding to P=1,500 μm, L=20 cm, IFPS=1 fps, SN=1,000, such as used in radiographic megavoltage imaging, $$\tau \lesssim \sim 1090 \ \mu s$$

- For a high resolution, large array, operated in radiographic mode with a long integration period giving a very high signal-to-noise, corresponding to P=400 μm, L=50 cm, IFPS=1 fps, SN=10,000, such as used in radiographic megavoltage imaging, $$\tau \lesssim \sim 87 \ \mu s$$

For radiotherapy:
- for tracking of a scanning radiotherapy beam:
  - the pitch, P, will range from 500 μm to 10,000 μm;
  - L will be as above;
  - the frame rate, IFPS, will range from ~500 frames per second to ~1 frame per second;
  - SN will range from ~10 to ~10,000.
  - Consequently, some limiting cases for the timing constant are:
  - For a high resolution, very large array, operated at a high frame rate, with a low signal-to-noise corresponding, to P=1,000 μm, L=60 cm, IFPS=500 fps, SN=100, $$\tau \lesssim \sim 0.7 \ \mu s$$

- For a high resolution, small array, operated at a high frame rate, with a low signal-to-noise corresponding to P=1,000 μm, L=20 cm, IFPS=500 fps, SN=10, $$\tau \lesssim \sim 4.3 \ \mu s$$

- For a low resolution, small array, operated at a low frame rate, with a high signal-to-noise, corresponding to P=10,000 μm, L=20 cm, IFPS=1 fps, SN=10,000, $$\tau \lesssim \sim 5430 \ \mu s$$

- For a high resolution, small array, operated at a high frame rate, with a low signal-to-noise, corresponding to P=1000 μm, L=25 cm, IFPS=500 fps, SN=10, $$\tau \lesssim \sim 3.5 \ \mu s$$

For diagnostic imaging:
- the pitch P will range from ~25 μm to ~500 μm
- the length of a side of the sensitive region of the array, L, will range from ~2 cm to ~60 cm;
- in fluoroscopic mode, the frame rate will range from ~120 frames per second to ~1 frame per second. In radiographic mode, the irradiation period for an image will range from ~1 μs to ~10 seconds. However, in radiographic mode at the end of an irradiation period, it is desirable to actually perform the readout of the array in ~1.0 second. This is sufficiently fast that, along with the time required by the interfacing electronics and imaging workstation, the image may be presented within several seconds of the irradiation. In fluoroscopic imaging, IFPS is equal to the actual frame rate while in radiographic imaging, IFPS is equal to ~1.0 fps.
- SN will range from ~10 to ~10,000.
- Consequently, some limiting cases for the time constant are:
  - For a very high resolution, moderately large array, operated in radiographic mode, with a reasonable signal-to-noise, corresponding to P=25 μm, L=30 cm, IFPS=1 fps, SN=1,000, such as used for radiographic breast imaging, $$\tau \leq \sim 12 \ \mu s$$

- For a very high resolution, moderately large array, operated in radiographic mode, with a high signal-to-noise, corresponding to P=25 μm, L=30 cm, IFPS=1 fps, SN=10,000, such as used for radiographic breast imaging, $$\tau \leq \sim 9 \ \mu s$$

- For a moderately low resolution, small array, operated at a very high frame rate, with a reasonable signal-to-noise, corresponding to P=200 μm, L=25 cm, IFPS=120 fps, SN=1,000, such as used for fluoroscopic-cardiac imaging, $$\tau \leq \sim 1.0 \ \mu s$$

- For a moderately low resolution, small array, operated at a very high frame rate, with a very high signal-to-noise, corresponding to P=200 μm, L=25 cm, IFPS=120 fps, SN=10,000, such as used for fluoroscopic cardiac imaging, $$\rho \leq \sim 0.7 \ \mu s$$

- For a high resolution, large array, operated in radiographic mode, with a high signal-to-noise, corresponding to P=100 μm, L=43 cm, IFPS=1 fps, SN=1,000, such as used for radiographic chest imaging, $$\tau \leq \sim 34 \ \mu s$$

- For a high resolution, large array, operated in radiographic mode, with a very high signal-to-noise, corresponding to P=100 μm, L=43 cm, IFPS=1 fps, SN=10,000, such as used for radiographic cardiac imaging, $$\tau \leq \sim 25 \ \mu s$$

- For a low resolution, small array, operated at a low frame rate, with a high signal-to-noise, corresponding to P=500 μm, L=25 cm, IFPS=1 fps, SN=1,000, such as used for general fluoroscopy, $$\tau \leq \sim 290 \ \mu s$$

- For a low resolution, small array, operated at a low frame rate, with a low signal-to-noise, corresponding to P=500 μm, L=25 cm, IFPS=1 fps, SN=100, such as used for general fluoroscopy, $$\tau \leq \sim 434 \ \mu s$$

- For a low resolution, small array, operated at a high frame rate, with a high signal-to-noise, corresponding to P=500 μm, L=25 cm, IFPS=60 fps, SN=1,000, such as used for general fluoroscopy, $$\tau \leq \sim 4.8 \ \mu s$$

- For a high resolution, small array, operated at a high frame rate, with a high signal-to-noise, corresponding to P=100 μm, L=25 cm, IFPS=60 fps, SN=1,000, such as used for general fluoroscopy, $$\tau \leq \sim 1.0 \ \mu s$$

- For a high resolution, small array, operated at a low frame rate, with a high signal-to-noise, corresponding to P=100 μm, L=25 cm, IFPS=1 fps, SN=1,000, such as used for general fluoroscopy, $$\tau \leq \sim 58 \ \mu s$$

- For a high resolution, large array, operated at a low frame rate, with a high signal-to-noise, corresponding to P=100 μm, L=60 cm, IFPS=1 fps, SN=1,000, such as used for general fluoroscopy, $$\tau \leq \sim 24 \ \mu s$$

- For a high resolution, large array, operated at a high frame rate, with a high signal-to-noise, corresponding to P=100 μm, L=60 cm, IFPS=60 fps, SN=1,000, such as used for general fluoroscopy, $$\tau \leq \sim 0.40 \ \mu s$$

- For a very high resolution, very small array, operated in radiographic mode, with a high signal-to-noise corresponding to P=25 μm, L=2 cm, IFPS=1 fps, SN=1000, such as used for dental radiographic imaging, $$\tau \leq \sim 181 \ \mu sec$$

Summarizing, for the various anticipated applications:

| |
|---|
| ~25 ≤ P ≤ 10,000 (μm) |
| ~2 ≤ L ≤ 60 (cm) |
| ~1 ≤ IFPS ≤ ~500 (fps) |
| ~10 ≤ SN ≤ ~10,000 |

The present invention makes possible the detection of the centroid of the megavoltage radiation beam as many times per second as there are radiation bursts and the determination of the transmitted radiation dose on a burst-by-burst basis. Further, the present invention verifies the radiation dose is directed upon the desired target area. The present invention achieves a superior signal-to-noise ratio and receives enough information for a megavoltage image to be formed in 0.10 seconds, (10 images a second), the only limitation being the speed of the processing hardware.

The present invention may be used for years at a time without a degradation in performance due to continued exposure to megavoltage radiation. When there is some radiation damage to the array, a simple heat treatment at 130°–150° C. restores the original characteristics of the device.

The present invention allows the replacement of the bulky XRII unit with a thin, light, flat panel digital imaging system whose profile offers minimal obstruction, which is free of distortion, glare, and the effects of magnetic fields.

The present invention allows the replacement of x-ray film and scanning-laser-stimulated-luminescence systems which do not allow the possibility of real-time presentation of x-ray images and require relatively nonportable developing units or readers with a light, flat-panel digital imaging system allowing immediate real-time presentation of x-ray images with no need for a bulky developing unit or reader and which may be made portable.

Finally, the present invention allows the creation of combinations of imagers which are stacked one on top of the other. The various imagers in the stack may be optimized for various forms or imaging.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A real-time imaging device for use with an incident ionizing radiation beam, comprising:
   signal conversion means including an array of pixel sensors, each having a predetermined capacitance, for converting the incident ionizing radiation beam into an electron hole-pair signal and storing said signal at the plurality of pixel sensors; and
   switching means including a plurality of transistors, each having a predetermined resistance, wherein each of said plurality of transistors reads out the signal stored by an associated one of said plurality of pixel sensors, wherein the capacitance of one of the plurality of pixel sensors when multiplied by the resistance of an associated transistor yield a time constant, $\tau_{RC}$, in μsec which satisfies the following relationship, which thereby permits real-time imaging of said radiation beam, $$\tau_{RC} \leq \frac{100 \cdot P}{L \cdot IFPS \cdot \ln(SN)}$$

where
   P = the pixel-pixel pitch in μm, where $\sim 25 \leq P \leq \sim 10{,}000$,
   L = the length, in cm, of one column of pixels sensors of the array, where $\sim 2 \leq L \leq \sim 60$,
   IFPS = instantaneous frame rate per second which is the effective rate at which the array is being read-out, where $\sim 1 \leq IFPS \leq \sim 500$, and
   SN = the inverse of the degree to which each pixel sensor needs to be sampled and thus recharged, where $\sim 10 \leq SN \leq \sim 10{,}000$.

2. A device according to claim 1, further comprising:
   means for generating a megavoltage radiation beam or diagnostic x-ray beam as said incident ionizing radiation beam.

3. A device according to claim 1, wherein the plurality of transistors are thin film field effect transistors.

4. A device according to claim 1, wherein said plurality of transistors are fabricated of polycrystalline silicon.

5. A device according to claim 1, wherein said pixel sensors comprise:
   means for converting said radiation beam to visible light; and
   plural photosensitive sensors formed of a material selected from the group consisting of a-Si$_x$C$_{1-x}$:H, $0 < x < 1$; a-Si$_y$Ge$_{1-y}$:H, $0 < y < 1$; a-Si.H; and microcrystalline silicon, each sensor having oppositely doped exterior layers sandwiching an intrinsic layer to define a structure selected from the group consisting of a p-i-n structure and an n-i-p structure.

6. A device according to claim 5, wherein said plural photosensitive pixel sensors comprise:
   sensors, having facing said converting means, a layer selected from the group consisting of a doped a-Si:H layer, a doped Si$_x$:C$_{1-x}$:H layer and a doped microcrystalline silicon layer.

7. A device according to claim 6, wherein each transistor is located vertically beneath, relative to the side of the sensor facing the incident ionizing radiation beam, the respective sensor associated therewith.

8. A device according to claim 5, further comprising:
   bias means for applying a reverse bias to said photosensitive pixel sensors.

9. A device according to claim 5, wherein each transistor is located vertically beneath, relative to the side of the sensor facing the incident ionizing radiation beam, the respective sensor associated therewith.

10. A device according to claim 1, wherein said pixel sensors comprise:
    thick a-Si.H diodes.

11. A device according to claim 10, wherein each transistor is located vertically beneath, relative to the side of the sensor facing the incident ionizing radiation beam, the respective sensor associated therewith.

12. A device according to claim 1, wherein said pixel sensors comprise: a thick layer of chalogenide glass.

13. A device according to claim 12, wherein each transistor is located vertically beneath, relative to the side of the sensor facing the incident ionizing radiation beam, the respective sensor associated therewith.

14. A device according to claim 1, wherein each transistor is located vertically beneath, relative to the side of the sensor facing the incident ionizing radiation beam, the respective sensor associated therewith.

15. A real-time imaging device for storing and retrieving an imaging signal resulting from incident ionizing radiation bursts, comprising:
    a scintillation layer;
    an array of photosensitive pixel sensors optically coupled to the scintillation layer, each photosensitive sensor having a first semiconductor layer doped to a first conductivity type, a second semiconductor layer doped to a second conductivity type, and an intrinsic second semiconductor layers; and
    a plurality of transistors, each having a predetermined resistance, connected to respective of said photosensitive sensors for reading out the stored signal, each photosensitive sensor and the respective transistor connected thereto forming one pixel, wherein the capacitance of each of the photosensitive sensors when multiplied by the resistance of said respective transistor yield a time constant $\tau_{RC}$, in μsec which satisfies the following relationship and which thereby permits real-time imaging of said incident radiation bursts, $$\tau_{RC} \leq \frac{100 \cdot P}{L \cdot IFPS \cdot \ln(SN)}$$

where
P = the pixel-pixel pitch in μm, where $\sim 25 \leq p \leq \sim 10{,}000$,
L = the length, in cm, of one column of pixels sensors of the array, where $\sim 2 \leq L \leq \sim 60$,
IFPS = instantaneous frame ratio per second which is the effective rate at which the array is being read-out, where $\sim 1 \leq IFPS \leq \sim 500$, and
SN = the inverse of the degree of which each pixel sensor needs to be sampled and thus recharged, where $\sim 10 \leq SN \leq \sim 10{,}000$.

16. A device according to claim 15, wherein said photosensitive pixel sensors comprise:
plural sensors formed of a material selected from the group consisting of a-Si$_x$C$_{1-x}$:H, $0<x<1$; a-Si$_y$Ge$_{1-y}$:H, $0<y<1$; a-Si:H; and microcrystalline silicon; each sensor having oppositely doped exterior layers sandwiching an intrinsic layer to define a structure selected from the group consisting of a p-i-n structure and an n-i-p structure.

17. A device according to claim 16, wherein said plural photosensitive pixel sensors comprise:
sensors, having facing said conversion means, a layer selected from the group consisting of a doped a-Si:H layer, a doped Si$_x$:C$_{1-x}$:H layer and a doped microcrystalline silicon layer.

18. A real-time imaging device according to claim 16, further comprising:
a conversion layer for converting photons from the radiation bursts into electrons, said scintillation layer converting the electrons created in the conversion layer to visible light, and
means for generating megavoltage radiation bursts as said incident radiation bursts.

19. A device according to claim 16, further comprising:
bias means for applying a reverse bias to said photosensitive pixel sensors.

20. A device according to claim 15, wherein each transistor is a thin film field effect transistor.

21. A device according to claim 20, further comprising:
an upper electrode layer transparent to the visible light so as to allow the visible light from the scintillation layer to pass therethrough;
a lower electrode layer; and
wherein said photosensitive sensors are located between the upper and lower electrode layers.

22. A device according to claim 20, wherein each said thin film field effect transistor comprises:
a gate contact region;
a gate dielectric layer placed over the gate contact region;
an a-Si:H layer placed over the gate dielectric layer;
a second dielectric layer located directly above the gate contact region and connected to the a-Si:H layer;
a first doped a-Si:H source region and a second doped a-Si:H drain region connected to selected portions of said a-Si:H layer and positioned on opposed sides of the gate contact region and separated by said second dielectric layer;
a drain contact in contact with said second doped region; and
a source contact in contact with said first doped region.

23. A device according to claim 22, wherein:
the source contact is connected to the lower electrode layer.

24. A device according to claim 23, further comprising:
a gate select line located in a given row of the array and connected to the gate of each thin-film field effect transistor of said plurality of transistors in the given row.

25. A device according to claim 24, further comprising:
a shielded housing enclosing said array of sensors.

26. A device according to claim 25, comprising:
said shielded housing comprising a photon-to-electron conversion layer; and
a scintillation layer formed over said photon-to-electron conversion layer connected to the upper electrode layer atop each sensor of said plurality of sensors.

27. A device for storing and retrieving an imaging signal obtained as result of diagnostic X-rays for purposes of realizing real-time images, comprising:
an array of a plurality of photosensitive pixel sensors arranged in rows and columns;
each of said sensors having a first semiconductor layer doped to a first conductivity type, a second semiconductor layer doped to a second conductivity type, and an intrinsic layer sandwiched between said first and second semiconductor layers;
an upper electrode layer transparent to visible light connected atop said first semiconductor layer of each of said sensors;
a lower electrode layer connected below said second semiconductor layer of each of said sensors; and
a plurality of thin film field effect transistors each having a predetermined resistance, each of which is connected to a respective of said plurality of sensors for reading out an imaging signal stored in said respective sensor upon irradiation by said diagnostic X-rays, each combination of sensor connected to a respective transistor corresponding to one pixel, wherein the capacitance of each sensor when multiplied by the resistance of the respective transistor to which said sensor is connected yield a time constant, $\tau_{RC}$, in μsec which satisfies the following relationship and which thereby permits real-time imaging of said diagnostic X-rays, $$\tau_{RC} \leq \frac{100 \cdot P}{L \cdot IFPS \cdot \ln(SN)}$$

where
P = the pixel-pixel pitch in μm, where $\sim 25 \leq P \leq \sim 10{,}000$,
L = the length, in cm, of one column of pixels sensors of the array, where $\sim 2 \leq L \leq \sim 60$,
IFPS = instantaneous frame rate per second which is the effective rate at which the array is being read-out, where $\sim 1 \leq IFPS \leq \sim 500$, and
SN = the inverse of the degree to which each pixel sensor needs to be sampled and thus recharged, where $\sim 10 \leq SN \leq \sim 10{,}000$.

28. A device according to claim 27, wherein each thin film field effect transistor of said plurality of transistors comprises:
- a gate contact region;
- a gate dielectric layer placed over the gate contact region;
- an a-Si:H layer placed over the gate dielectric layer;
- a second dielectric layer located directly above the gate contact region and connected to the a-Si:H layer;
- a first doped a-Si:H source region and a second doped a-Si:H drain region connected to selected portions of said a-Si:H layer and positioned on opposed sides of the gate contact region and separated by said second dielectric layer;
- a drain contact in contact with said second doped region; and
- a source contact in contact with said first doped region.

29. A device according to claim 28, comprising:
- a lower electrode layer integrally formed with said source contact.

30. A device according to claim 29, further comprising:
- a biasing line located in a given column of the array and connected to the upper electrode layer atop the first a-Si:H layer of each sensor of said plurality of sensors in the given column.

31. A device according to claim 30 further comprising:
- a signal line located in the given column of the array and connected to the drain of each thin-film field effect transistor of said plurality of transistors in the given column.

32. A real-time imaging device having a plurality of arrays one stacked upon the other, with each array of said plurality of arrays having a plurality of sensors arranged in rows and columns, each sensor of each array comprising:
- a scintillation layer to convert incident radiation signals into a visible light signal;
- a photosensitive element comprising a first semiconductor layer doped to a first conductivity type, a second semiconductor layer doped to a second conductivity type, and an intrinsic layer sandwiched between said first and second semiconductor layers;
- a thin film field effect transistor, connected to said photosensitive element and formed upon a common substrate with said photosensitive element, for reading out a signal from said element, said transistor and respective photosensitive element forming one pixel, wherein a capacitance of each photosensitive element when multiplied by a resistance of the transistor connected thereto yield a time constant, $\tau_{RC}$, in $\mu$sec which satisfies the following relationship and which thereby permits real-time imaging of said incident relation signals, $$\tau_{RC} \leq \frac{100 \cdot P}{L \cdot IFPS \cdot \ln(SN)}$$

where
- P = the pixel-pixel pitch in $\mu$m, where $\sim 25 \leq P \leq \sim 10,000$,
- L = the length, in cm, of one column of pixels sensors of the array, where $\sim 2 \leq L \leq \sim 60$,
- IFPS = instantaneous frame rate per second which is the effective rate at which the array is being read-out, where $\sim 1 \leq IFPS \leq \sim 500$, and
- SN = the inverse of the degree to which each pixel sensor needs to be sampled and thus recharged, where $\sim 10 \leq SN \leq \sim 10,000$.

33. A device according to claim 32, further comprising:
- bias means for applying a reverse bias to each said photosensitive element.

* * * * *

UNITED STATES PATENT AND TRADEMARK OFFICE
CERTIFICATE OF CORRECTION

PATENT NO. : 5,262,649
DATED : November 16, 1993
INVENTOR(S) : Larry E. Antonuk, et al It is certified that error appears in the above-indentified patent and that said Letters Patent is hereby corrected as shown below:

Column 1, Line 53, "During simulation" should read --During simulation,--

Column 9, Line 15, "for neither a" should read --for either a--

Column 10, Line 9, "a film cassette" should read --a film cassette.--.

Column 21, Line 44, "stringent requirement For" should read --stringent requirement.  For--

Column 23, Line 41, "$\rho \leq \sim 0.7\ \mu s$" should read --$\tau \leq \sim 0.7\ \mu s$--

Signed and Sealed this

Seventh Day of March, 1995

Attest:

BRUCE LEHMAN

*Attesting Officer*   *Commissioner of Patents and Trademarks*